(12) United States Patent
Tiongson et al.

(10) Patent No.: US 12,042,194 B2
(45) Date of Patent: Jul. 23, 2024

(54) BONE STABILIZATION SYSTEMS

(71) Applicant: GLOBUS MEDICAL, INC., Audubon, PA (US)

(72) Inventors: Christina M. Tiongson, Norristown, PA (US); David R. Jansen, Glenmoore, PA (US)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 18/170,166

(22) Filed: Feb. 16, 2023

(65) Prior Publication Data

US 2023/0190346 A1  Jun. 22, 2023

Related U.S. Application Data

(63) Continuation of application No. 17/092,766, filed on Nov. 9, 2020, now Pat. No. 11,607,254, which is a continuation of application No. 15/925,846, filed on Mar. 20, 2018, now Pat. No. 10,856,920, which is a continuation-in-part of application No. 15/703,345, filed on Sep. 13, 2017, now abandoned.

(51) Int. Cl.
| | |
|---|---|
| A61B 17/80 | (2006.01) |
| A61B 17/17 | (2006.01) |
| A61B 17/68 | (2006.01) |
| A61B 17/70 | (2006.01) |

(52) U.S. Cl.
CPC ...... *A61B 17/8085* (2013.01); *A61B 17/1728* (2013.01); *A61B 17/683* (2013.01); *A61B 17/7011* (2013.01); *A61B 17/8014* (2013.01); *A61B 17/8052* (2013.01); *A61B 17/8057* (2013.01); *A61B 17/8061* (2013.01); *A61B 2017/681* (2013.01)

(58) Field of Classification Search
CPC .......................... A61B 17/80; A61B 17/8061
See application file for complete search history.

(56) References Cited

U.S. PATENT DOCUMENTS

| | | | |
|---|---|---|---|
| 1,105,105 | A | 7/1914 | Sherman |
| 2,486,303 | A | 10/1949 | Longfellow |
| 3,716,050 | A | 2/1973 | Johnston |
| 4,493,317 | A | 1/1985 | Klaue |
| 4,524,765 | A | 6/1985 | de Zbikowski |
| 4,651,724 | A | 3/1987 | Berentey et al. |
| 4,683,878 | A | 8/1987 | Carter |
| 4,781,183 | A | 11/1988 | Casey et al. |

(Continued)

FOREIGN PATENT DOCUMENTS

| | | |
|---|---|---|
| CA | 2933020 A1 | 6/2016 |
| CN | 2003210478 A | 7/2003 |

(Continued)

*Primary Examiner* — Olivia C Chang

(57) ABSTRACT

Bone plates for engaging bone members are described herein. The bone plates can receive one or more screws to secure the bone plates to an underlying bone member. The one or more screws can be inserted into bone plate holes that can be considered locking or non-locking. The bone plates described herein can have particular combinations of locking and/or non-locking holes. The bone plates can include features that accommodate the underlying anatomy of different types of bone, such as the condylar region of a femur.

20 Claims, 14 Drawing Sheets

(56) References Cited

U.S. PATENT DOCUMENTS

| | | |
|---|---|---|
| 4,867,144 A | 9/1989 | Karas et al. |
| 4,923,471 A | 5/1990 | Morgan |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,423,826 A | 6/1995 | Coates et al. |
| 5,468,242 A | 11/1995 | Reisberg |
| D365,634 S | 12/1995 | Morgan |
| 5,489,305 A | 2/1996 | Morgan |
| 5,527,311 A | 6/1996 | Procter et al. |
| 5,578,036 A | 11/1996 | Stone et al. |
| 5,601,553 A | 2/1997 | Trebing et al. |
| 5,676,667 A | 10/1997 | Hausman |
| 5,690,631 A | 11/1997 | Duncan et al. |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,746,742 A | 5/1998 | Runciman et al. |
| 5,766,175 A | 6/1998 | Martinotti |
| 5,785,712 A | 7/1998 | Runciman et al. |
| 5,797,914 A | 8/1998 | Leibinger |
| 5,814,048 A | 9/1998 | Morgan |
| 5,925,048 A | 7/1999 | Ahmad et al. |
| 5,938,664 A | 8/1999 | Winquist et al. |
| 5,961,519 A | 10/1999 | Bruce et al. |
| 6,001,099 A | 12/1999 | Huebner |
| 6,093,201 A | 7/2000 | Cooper et al. |
| 6,096,040 A | 8/2000 | Esser |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| 6,533,786 B1 | 3/2003 | Needham et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 | 7/2007 | Orbay |
| 7,294,130 B2 | 11/2007 | Orbay |
| 7,322,983 B2 | 1/2008 | Harris |
| 7,341,589 B2 | 3/2008 | Weaver et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niedernberger et al. |
| 7,695,472 B2 | 4/2010 | Young |
| 7,717,946 B2 | 5/2010 | Oepen et al. |
| 7,722,653 B2 | 5/2010 | Young et al. |
| 7,740,648 B2 | 6/2010 | Young et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,540,755 B2 | 9/2013 | Whitmore |
| 8,551,095 B2 | 10/2013 | Fritzinger et al. |
| 8,568,462 B2 | 10/2013 | Sixto, Jr. et al. |
| 8,574,268 B2 | 11/2013 | Chan et al. |
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |

(56) References Cited

U.S. PATENT DOCUMENTS

| | | |
|---|---|---|
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama |
| 9,370,388 B2 | 6/2016 | Globerman et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,549,819 B1 | 1/2017 | Bravo et al. |
| 9,566,097 B2 | 2/2017 | Fierlbeck et al. |
| 9,622,799 B2 | 4/2017 | Orbay et al. |
| 9,636,157 B2 | 5/2017 | Medoff |
| 9,649,141 B2 | 5/2017 | Raven, III et al. |
| 9,668,794 B2 | 6/2017 | Kuster et al. |
| 9,801,670 B2 | 10/2017 | Hashmi et al. |
| 11,096,730 B2 | 8/2021 | Tiongson et al. |
| 2002/0045901 A1 | 4/2002 | Wagner et al. |
| 2003/0040752 A1 | 2/2003 | Kitchens |
| 2004/0097937 A1 | 5/2004 | Pike et al. |
| 2005/0049594 A1 | 3/2005 | Wack et al. |
| 2005/0107796 A1 | 5/2005 | Gerlach et al. |
| 2005/0131413 A1 | 6/2005 | O'Driscoll et al. |
| 2005/0159753 A1 | 7/2005 | Kitchens |
| 2005/0187551 A1 | 8/2005 | Orbay et al. |
| 2006/0095044 A1 | 5/2006 | Grady et al. |
| 2006/0149265 A1 | 7/2006 | James et al. |
| 2006/0241607 A1 | 10/2006 | Myerson et al. |
| 2007/0162016 A1 | 7/2007 | Matityahu |
| 2007/0173840 A1 | 7/2007 | Huebner |
| 2007/0270849 A1 | 11/2007 | Orbay et al. |
| 2007/0288022 A1 | 12/2007 | Lutz |
| 2008/0021477 A1 | 1/2008 | Strnad et al. |
| 2008/0195240 A1 | 8/2008 | Martin et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0299369 A1 | 12/2009 | Orbay et al. |
| 2009/0312760 A1 | 12/2009 | Forstein et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0137873 A1 | 6/2010 | Grady, Jr. |
| 2010/0274247 A1 | 10/2010 | Grady, Jr. et al. |
| 2011/0106086 A1 | 5/2011 | Laird |
| 2011/0137314 A1 | 6/2011 | Kuster et al. |
| 2011/0166573 A1* | 7/2011 | Wenk ............. A61B 17/1728 606/71 |
| 2011/0218580 A1 | 9/2011 | Schwager et al. |
| 2012/0010667 A1 | 1/2012 | Eglseder |
| 2012/0059424 A1 | 3/2012 | Epperly et al. |
| 2012/0203227 A1 | 8/2012 | Martin |
| 2012/0232599 A1 | 9/2012 | Schoenly et al. |
| 2012/0323284 A1 | 12/2012 | Baker et al. |
| 2013/0018426 A1 | 1/2013 | Tsai et al. |
| 2013/0046347 A1 | 2/2013 | Cheng et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2013/0289630 A1 | 10/2013 | Fritzinger |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0066998 A1 | 3/2014 | Martin |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0243901 A1 | 8/2014 | Mebarak et al. |
| 2014/0277178 A1 | 9/2014 | O'Kane et al. |
| 2014/0277181 A1 | 9/2014 | Garlock |
| 2014/0316473 A1 | 10/2014 | Pfeffer |
| 2014/0330320 A1 | 11/2014 | Wolter |
| 2014/0378975 A1 | 12/2014 | Castaneda et al. |
| 2015/0005831 A1 | 1/2015 | Sands |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0157337 A1 | 6/2015 | Wolf et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223824 A1 | 8/2015 | Mebarak |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2015/0374421 A1 | 12/2015 | Rocci et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0183990 A1 | 6/2016 | Koizumi et al. |
| 2016/0262814 A1 | 9/2016 | Wainscott |
| 2016/0278828 A1 | 9/2016 | Ragghianti |
| 2016/0310183 A1 | 10/2016 | Shaw et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0105775 A1 | 4/2017 | Ricker et al. |

(56) References Cited

U.S. PATENT DOCUMENTS

| | | | |
|---|---|---|---|
| 2017/0215931 A1 | 8/2017 | Cremer et al. | |
| 2018/0289402 A1 | 10/2018 | Lueth et al. | |
| 2019/0076174 A1 | 3/2019 | Tiongson | |

FOREIGN PATENT DOCUMENTS

| | | |
|---|---|---|
| CN | 2846870 A1 | 5/2004 |
| CN | 2928259 A1 | 9/2009 |
| CN | 201987653 U | 9/2011 |
| CN | 202313691 U | 7/2012 |
| CN | 202821574 U | 3/2013 |
| CN | 202821575 U | 3/2013 |
| CN | 203506858 U | 4/2014 |
| CN | 203815563 U | 9/2014 |
| CN | 2016079504 A1 | 5/2016 |
| CN | 105982727 A | 10/2016 |
| EP | 1661525 A2 | 5/2006 |
| EP | 2730244 A1 | 5/2014 |
| JP | 2236010 A | 9/1990 |
| JP | 2008-518690 A | 6/2008 |
| JP | 2009-513268 A | 4/2009 |
| JP | 3177020 U | 6/2012 |
| JP | 2016-539737 A | 12/2016 |
| JP | 2020-11062 A | 1/2020 |
| TW | 201316942 A | 5/2013 |
| WO | 2007050796 A2 | 5/2007 |
| WO | 2007109302 A2 | 9/2007 |

\* cited by examiner

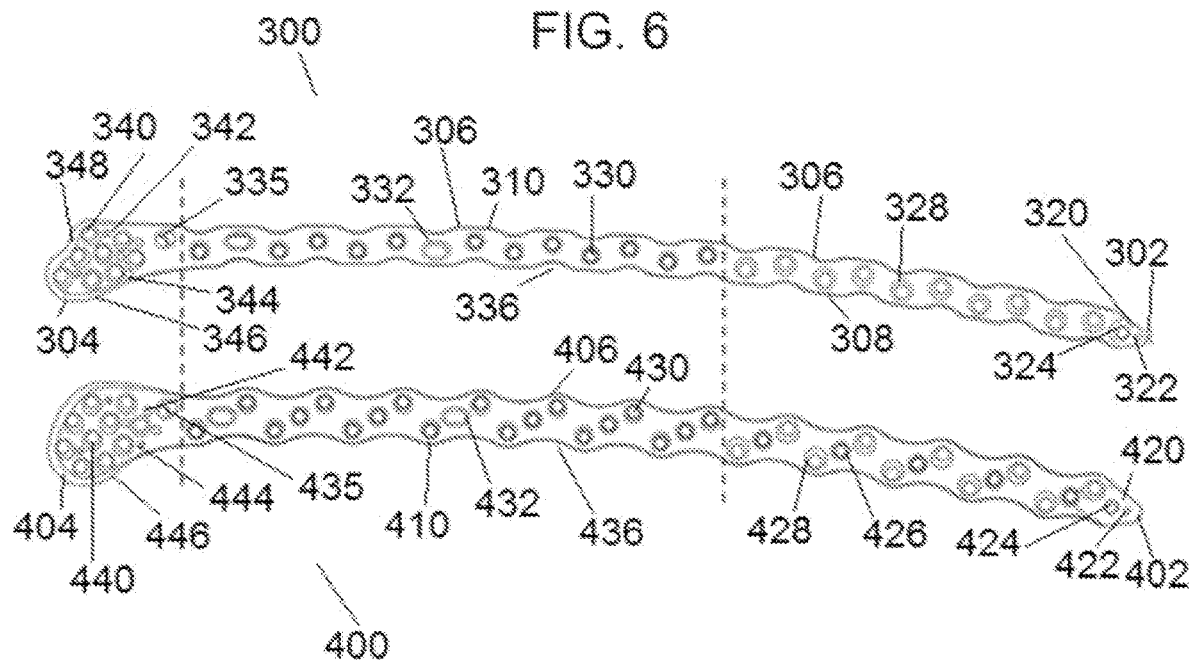

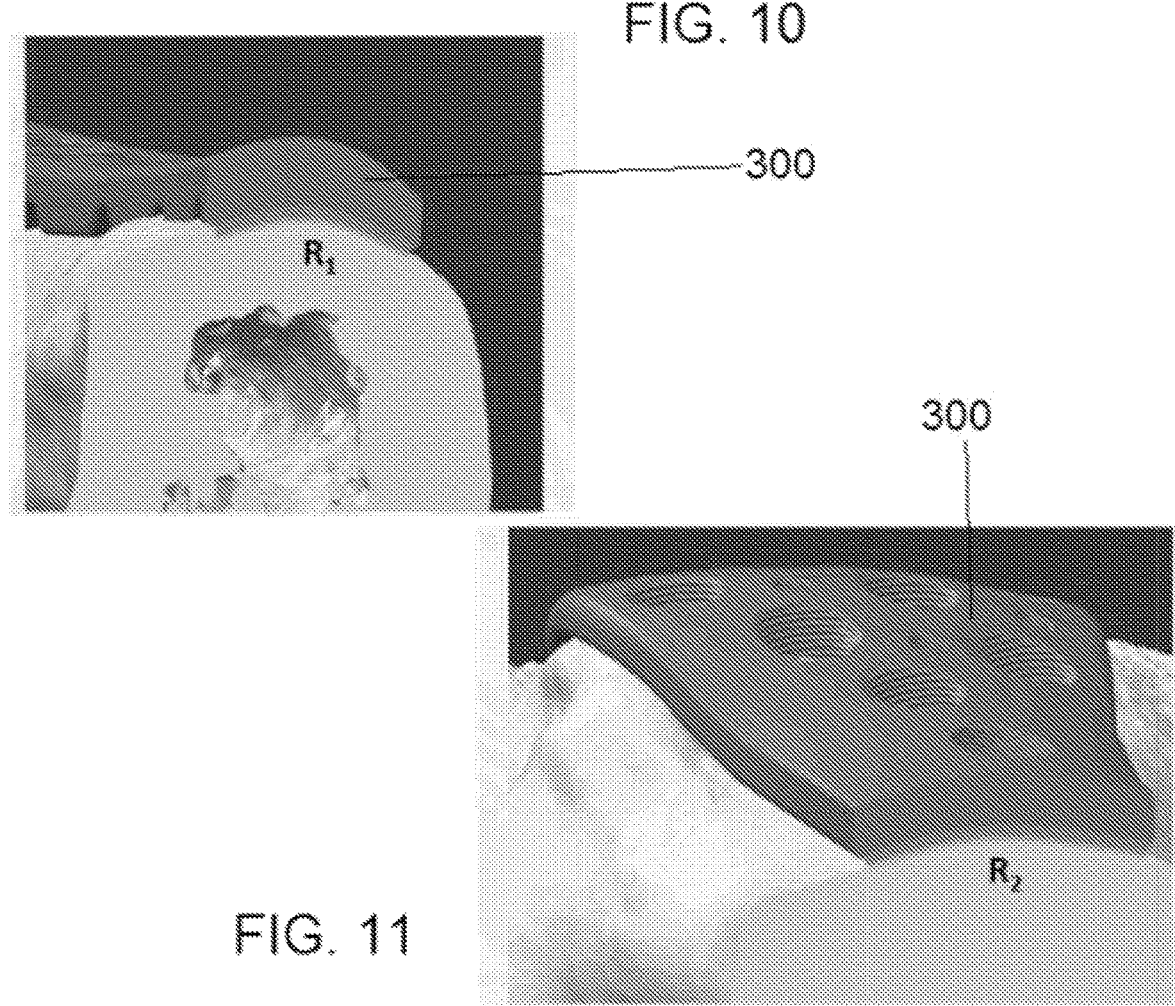

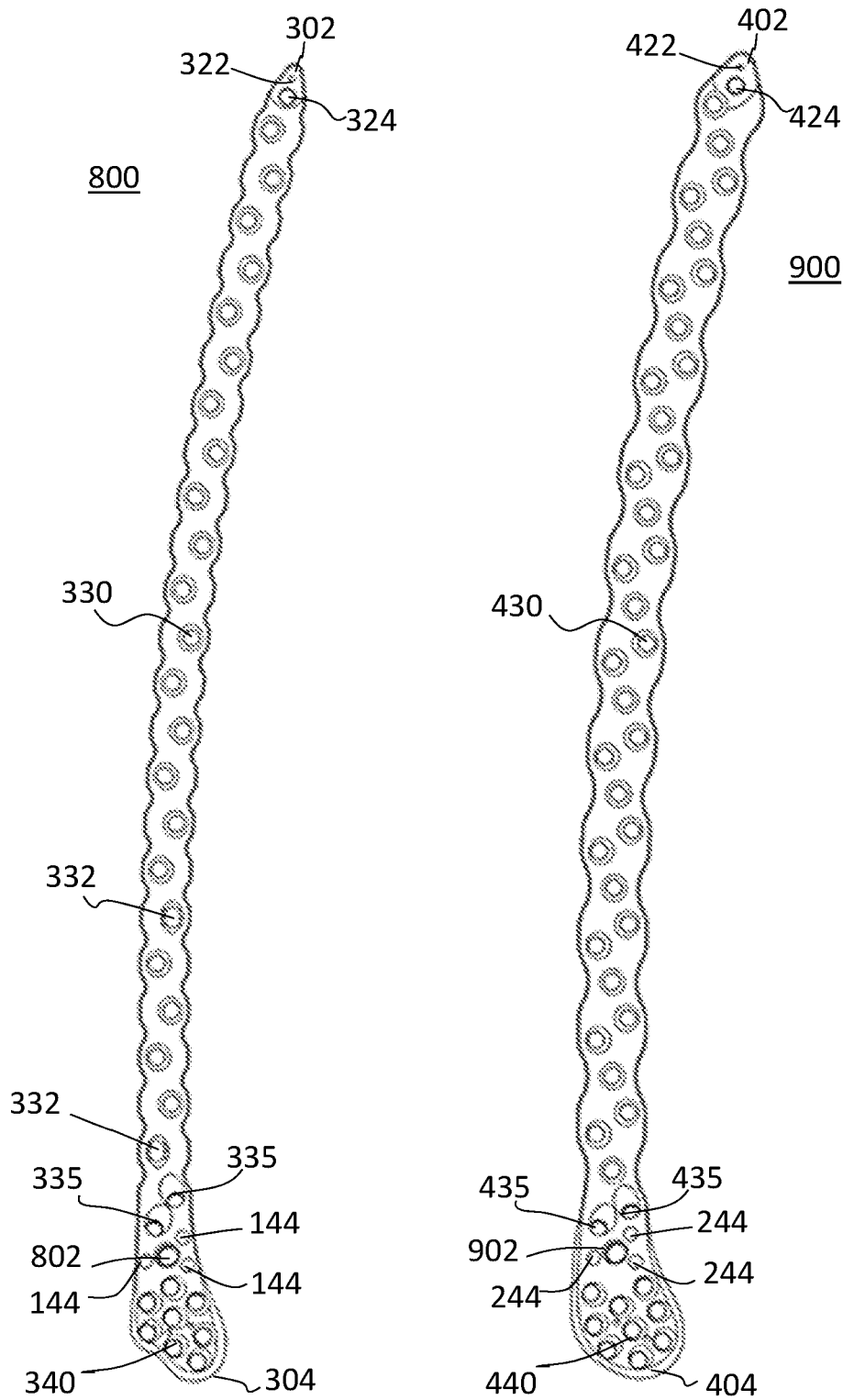

BONE STABILIZATION SYSTEMS

CROSS REFERENCE TO RELATED APPLICATIONS

This application is a continuation of U.S. patent application Ser. No. 17/092,766, filed on Nov. 9, 2020 (published as U.S. Pat. Pub. No. 2021-0052310), which is a continuation of U.S. patent application Ser. No. 15/925,846, filed on Mar. 20, 2018, now U.S. Pat. No. 10,856,920, which is a continuation-in-part of U.S. patent application Ser. No. 15/703,345 filed Sep. 13, 2017 (published as U.S. Pat. Pub. No. 2019-0076175), all of which are incorporated by reference herein in their entireties for all purposes.

FIELD OF THE INVENTION

The present disclosure relates to surgical devices, and more particularly, stabilization systems including plates, for example, for trauma applications.

BACKGROUND OF THE INVENTION

Bone fractures can be healed using plating systems. During treatment, one or more screws are placed on either side of a fracture, thereby causing compression and healing of the fracture. There is a need for improved plating systems as well as mechanisms for accurate use of the plating systems.

SUMMARY OF THE INVENTION

In accordance with the application, in some embodiments, a system is provided for treating a fracture in a bone. The system comprises a bone plate configured to engage the bone, the bone plate comprising a proximal portion, a shaft and a distal portion, wherein the proximal portion comprises a tapered tip, wherein the shaft comprises one or more holes, and wherein the distal portion comprises one or more distal holes and a posterior side and an anterior side, wherein the posterior side of the distal portion is raised relative to the anterior side of the distal portion. The system further comprises at least one fastener received through the one or more holes of the shaft and at least one fastener received through the one or more distal holes of the distal portion.

In other embodiments, a system is provided for treating a fracture in a bone. The system comprises a bone plate configured to engage the bone, the bone plate comprising a proximal portion, a shaft and a distal portion, wherein the proximal portion comprises a tapered tip, wherein the shaft comprises one or more holes, and wherein the distal portion comprises one or more distal holes and a posterior side and an anterior side, wherein the one or more holes in the shaft are fixed holes while the one or more distal holes in the distal shaft are polyaxial locking holes. The system further includes at least one fastener received through the one or more holes of the shaft and at least one fastener received through the one or more distal holes of the distal portion.

In yet another embodiment, a system for treating a fracture in a bone includes a bone plate configured to engage the bone, the bone plate extending along a longitudinal axis and comprising a proximal portion, a shaft, and a distal portion, the shaft comprises a plurality of holes (e.g., polyaxial holes), the plurality of holes include a first repeating pattern of holes and a second repeating pattern of holes, the first repeating pattern of holes having a first virtual line segment connecting center points of all of the first repeating pattern of holes, the second repeating pattern of holes having a second virtual line segment connecting center points of all of the second repeating pattern of holes, wherein the first virtual line segment and the second virtual line segment are parallel, and the first virtual line segment and the second virtual line segment are angled relative to the longitudinal axis, and the distal portion comprises a plurality of distal holes and a posterior side and an anterior side, wherein the posterior side of the distal portion is raised relative to the anterior side of the distal portion.

According to yet another embodiment, a system for treating a fracture in a bone includes a bone plate configured to engage the bone, the bone plate extending along a longitudinal axis and comprising a proximal portion, a shaft, and a distal portion, the shaft comprises a plurality of holes (e.g., polyaxial holes), the plurality of holes include a first repeating pattern of holes and a second repeating pattern of holes, the first repeating pattern of holes having a first virtual line segment connecting center points of all of the first repeating pattern of holes, the second repeating pattern of holes having a second virtual line segment connecting center points of all of the second repeating pattern of holes, wherein the first virtual line segment and the second virtual line segment are parallel, and the first virtual line segment and the second virtual line segment are angled relative to the longitudinal axis, and wherein the first repeating pattern includes a first center hole and the second repeating pattern includes a second center hole, and the center point of the first and second center holes are aligned generally along the longitudinal axis of the plate.

Also provided are kits including plates of varying shapes and sizes, bone anchors, fasteners, insertion tools, and components for installing the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 6 is a top view of a lengthened, narrow bone plate in accordance with some embodiments of the present application.

FIG. 7 is a top view of a lengthened, broad bone plate in accordance with some embodiments of the present application.

FIG. 10 is a cross-sectional view of a section of a representative plate showing an arced contour of an underside.

FIG. 11 is a cross-sectional view of a different section of a representative plate showing an arced contour of an underside.

FIG. 15 is a top view of another embodiment of a narrow bone plate.

FIG. 16 is a top view of another embodiment of a broad bone plate.

DETAILED DESCRIPTION OF THE INVENTION

Figure 1:
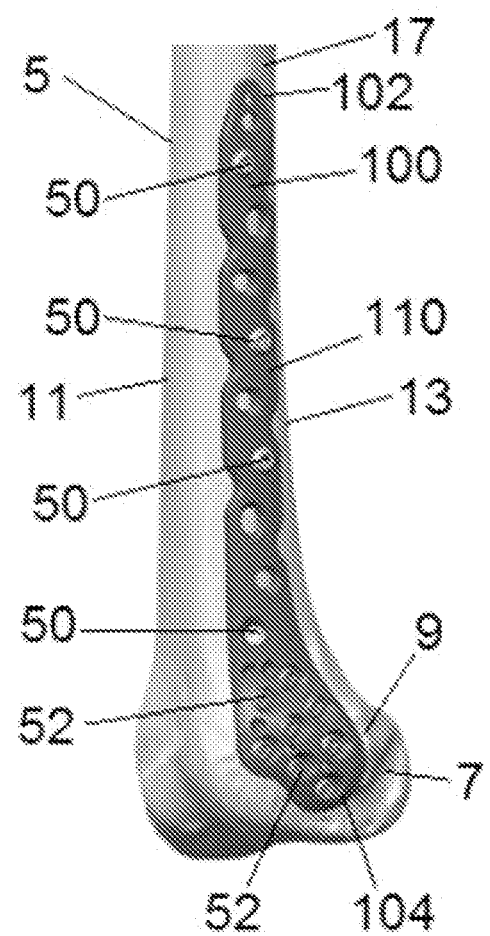
FIG. 1 is a view of a bone plate on bone in accordance with some embodiments of the present application.

Embodiments of the present application are generally directed to devices, systems and methods for bone stabilization. In particular, embodiments are directed to bone plates that extend across bone members to treat one or more fractures.

The plates described herein may be adapted to contact one or more of a femur, a distal tibia, a proximal tibia, a proximal humerus, a distal humerus, a clavicle, a fibula, an ulna, a radius, bones of the foot, bones of the hand, or other suitable bone or bones. The bone plates may be curved, contoured, straight, or flat. The plates may have a head portion that is contoured to match a particular bone surface, such as a condylar region, metaphysis or diaphysis. In addition, the plates may have a shaft portion that is contoured to match a particular surface that flares out in the form of an L-shape, T-shape, Y-shape. The plates may be adapted to secure small or large bone fragments, single or multiple bone fragments, or otherwise secure one or more fractures. In particular, the systems may include a series of trauma plates and screws designed for the fixation of fractures and fragments in diaphyseal and metaphyseal bone. Different bone plates may be used to treat various types and locations of fractures.

The bone plates may be comprised of titanium, stainless steel, cobalt chrome, carbon composite, plastic or polymer—such as polyetheretherketone (PEEK), polyethylene, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the bone plates may receive one or more screws or fasteners may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates and fasteners are made, it should be understood that bone plates and fasteners comprised of any appropriate material are contemplated.

The bone plates described herein can include a combination of locking holes and non-locking holes, only locking holes, or only non-locking holes. Locking holes comprise one or more openings that accept one or more locking fasteners. The one or more openings can be partially or fully threaded, thread-forming, or otherwise configured to allow locking attachment of the fastener to the hole. In some embodiments, the holes comprise stacked or polyaxial locking holes, which can accept both locking and non-locking fasteners. In some embodiments, the locking fasteners include heads that are at least partially threaded. The locking fasteners can be monoaxial or polyaxial. One non-limiting example of a locking fastener (among others) is shown in FIG. 6 of U.S. Ser. No. 15/405,368, filed Jan. 13, 2017, which is (along with any subsequent publication of the same application) hereby incorporated by reference in its entirety.

Figure 4:
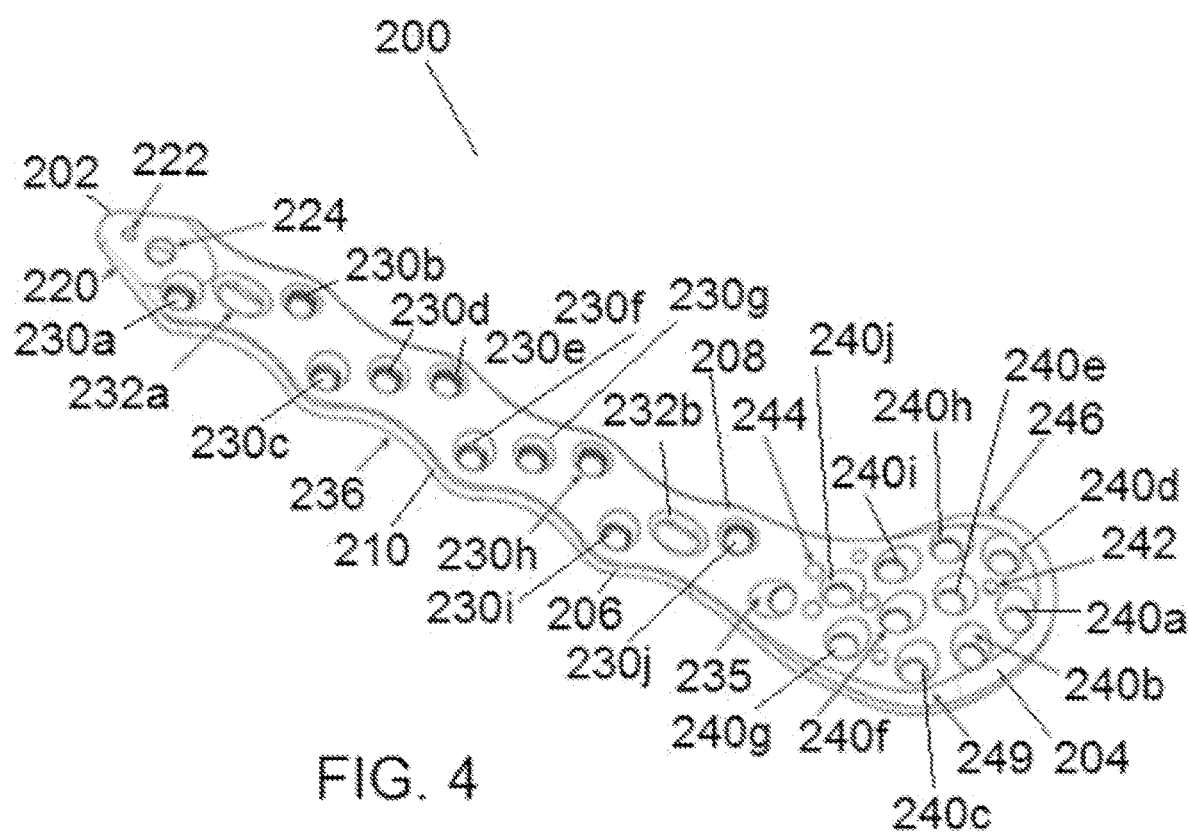
FIG. 4 is a top perspective view of a broad bone plate in accordance with some embodiments of the present application.

Non-locking holes comprise one or more openings for accepting one or more non-locking fasteners. The one or more openings are at least in part non-threaded. In some embodiments, these openings include non-threaded or stacked openings, which can accept both locking and non-locking fasteners. In some embodiments, the holes comprise stacked or polyaxial locking holes, which can accept both locking and non-locking fasteners. The non-locking fasteners can be monoaxial or polyaxial. One non-limiting example of a non-locking fastener (among others) is shown in FIG. 4 of U.S. Ser. No. 15/405,368, filed Jan. 13, 2017, which is (along with any subsequent publication of the same application) hereby incorporated by reference in its entirety. In some embodiments, the non-locking fasteners can include dynamic compression screws, which enable dynamic compression of an underlying bone.

In some embodiments, one or more of the plates described below include both locking and non-locking holes. Locking holes and locking fasteners may be useful for patients that have weaker bone. In addition, these may be helpful to prevent screw backout. Non-locking plates may be useful for patients that have strong bone.

In some embodiments, one or more of the plates described below can comprise improved distal femoral plates. These plates can be used by a surgeon as an internal fixation device for a variety of fracture patterns in the condylar region of the distal femur. Typical indications can include buttressing of comminuted/multi-fragmentary fractures, metaphyseal and supracondylar fractures, intra-articular and extra-articular femur fractures, periprosthetic fractures, fractures in osteopenic bone, osteotomies of the femur, and nonunions and malunions.

The one or more plates can provide a number of advantages, as will be discussed further below. In particular, the plates are designed to better accommodate anatomical features. For example, one or more plates can include a raised posterior sideline that accommodates an epicondylar protuberance. In addition, the plates have various holes or openings for receiving various types of screws or fasteners, such as one or more kickstand screws, fixed screws, and/or polyaxial screws, that provide excellent fixation while minimizing the risk of various deformities.

FIG. 1 is a view of a bone plate on bone in accordance with some embodiments of the present application. The bone plate 100 comprises a distal femur plate that is attached to a femur bone 5. The femur bone 5 comprises a distal condylar region 7 and a shaft 17 having a lateral side 11 and a medial side 13. The condylar region 7 includes a pair of medial and lateral condyles and a pair of medial and lateral epicondyles 9 positioned near the posterior edge of the condyles.

The bone plate 100 comprises a distal femur plate that comprises a proximal portion 102 and a distal portion 104.

The proximal portion 102 comprises a tapered insertion end that transitions into a shaft 110. The distal end of the shaft 110 flares out into a wider portion that forms the head or distal portion 104 of the bone plate 100. While the proximal portion 102 and shaft 110 of the bone plate 100 reside along the shaft 17 of the femur, the head or distal portion 104 of the bone plate 100 resides along the condylar region 7 of the femur.

Figure 2:
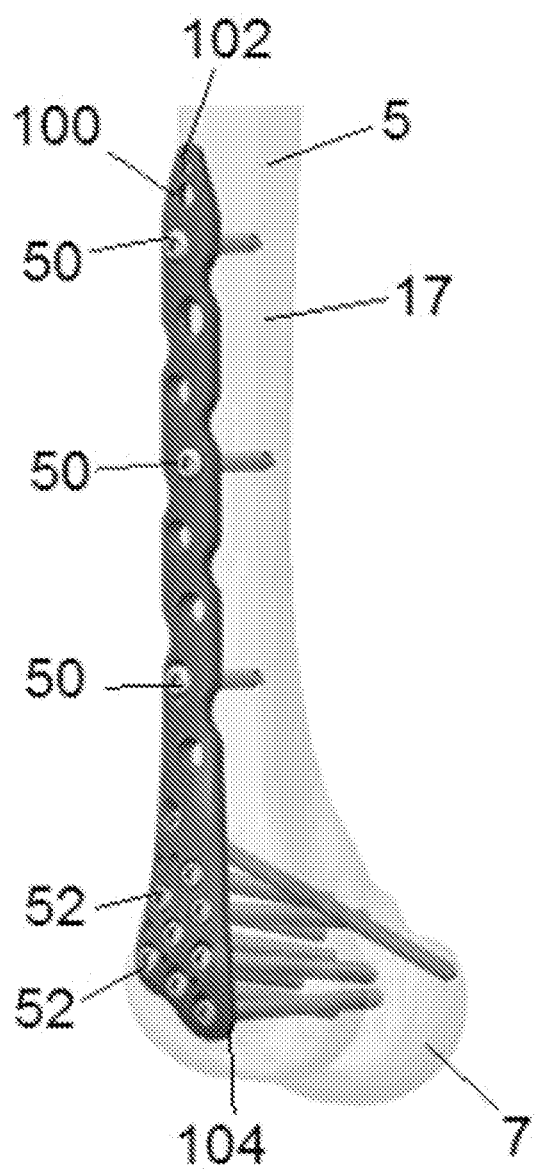
FIG. 2 is an alternate view of the bone plate on bone in FIG. 1.

The proximal portion 102 and shaft 110 of the bone plate 100 are configured to receive one or more screws or fasteners 50. Likewise, the distal portion 104 of the bone plate 100 is configured to receive one or more screws or fasteners 52. In some embodiments, the fasteners 50 on the proximal portion 102 and shaft 110 of the bone plate 100 comprise fixed angle fasteners, while the fasteners 52 on the distal portion 104 of the bone plate 100 comprise polyaxial fasteners. It has been found that while fixed angle fasteners are often stronger than polyaxial fasteners and provide greater stiffness to a bone plate attached to bone, at times, bone plate stiffness can be too great, thereby impeding proper bone healing. Accordingly, the present application provides a novel bone plate 100 that can accommodate both fixed angle fasteners 50 and polyaxial fasteners 52, thereby providing a balance between adequate stiffness and proper healing. In other embodiments, the bone plate 100 can receive only fixed angle fasteners, thereby providing a bone plate of increased stiffness. In other embodiments, the bone plate 100 can receive only variable angle fasteners, thereby providing a bone plate of less stiffness. Moreover, polyaxial locking holes provide an opportunity to place a fastener at a variety of different angles relative to the bone plate, permitting the avoidance of other fasteners and/or implants that may already be in the bone. Therefore, the polyaxial locking holes provide more options for a surgical user. FIG. 2 is an alternate view of the bone plate on bone in FIG. 1. From this view, one can see the bone plate 100 and its fasteners 50, 52 through the femur 5. As noted above, in some embodiments, fasteners 50 comprise fixed fasteners that enter through the shaft 17 of the femur 5. These fasteners 50 are shorter relative to fasteners 52 and provide increased stiffness. In some embodiments, fasteners 52 comprise variable angle fasteners that enter through the condylar region 7 of the femur 5. These fasteners 52 are longer relative to fasteners 50. While these fasteners 52 can provide decreased stiffness relative to the other fasteners 50, they also have more variability in their angle of placement relative to one another and the bone plate to provide more options for a surgical user.

Figure 3:
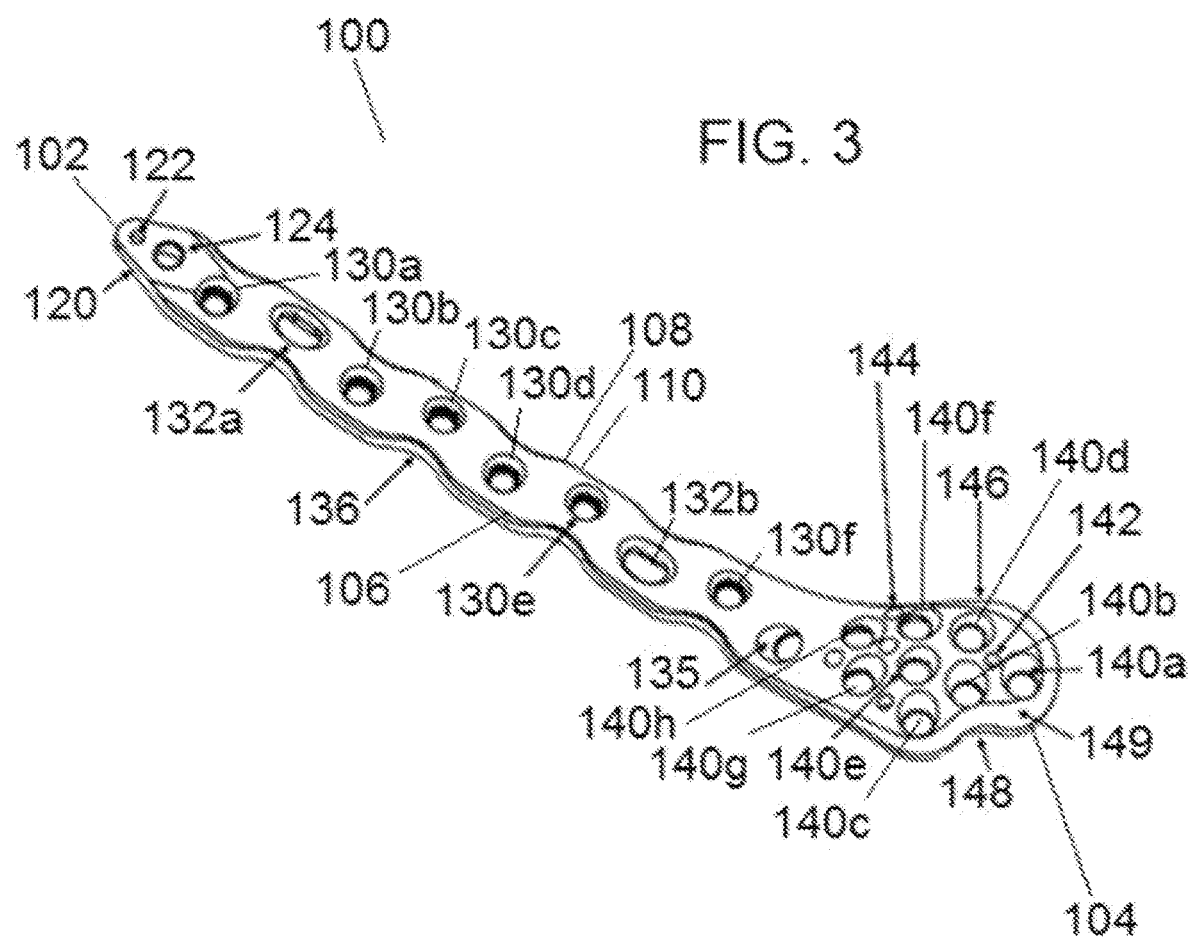
FIG. 3 is a top perspective view of a narrow bone plate in accordance with some embodiments of the present application.

FIG. 3 is a top perspective view of the narrow bone plate in accordance with some embodiments of the present application. The bone plate 100 comprises a proximal portion 102 and a distal portion 104. In between the proximal portion 102 and distal portion 104 is a shaft 110 having an anterior sidewall 106 and a posterior sidewall 108. Along the length of the bone plate 100 are a series of holes or openings for receiving screws or fasteners therein.

The proximal portion 102 of the bone plate 100 comprises a tapered tip 120. In some embodiments, the tapered tip 120 serves as the lead portion of the bone plate 100 to enter into an incision. In some embodiments, the tapered tip 120 allows for simplified submuscular plate insertion to minimize incision length. The proximal portion 102 further comprises a k-wire hole 122 for receiving a k-wire therein to guide bone plate 100 to a desired surgical site. The k-wire hole 122 allows for temporary fixation of the bone plate 100 to bone via a k-wire. In some embodiments, the k-wire hole 122 is unthreaded. In addition, the proximal portion 102 further comprises an articulated tensioning device (ATD) slot 124. The ATD slot 124 is configured to receive a portion of a tension or compression device (not shown) that can help to bring bone fragments together for healing. In some embodiments, the ATD slot 124 is composed of a through hole and a cylindrical shaped undercut on the bottom of the plate 100.

The proximal portion 102 transitions into the shaft portion 110. The shaft portion 110 comprises multiple holes or openings 130a, 130b, 130c, 130d, 130e, 130f that are configured to receive fasteners therein. In some embodiments, holes 130a-130f are configured to be fixed angle, stacked locking holes that can accommodate screws (e.g., between 3.5-7.5 mm screws, such as 4.5 mm screws). The fixed angle, stacked locking holes advantageously allow for mono-axial insertion of fasteners that lock to the bone plate 100. In some embodiments, these holes can also accommodate non-locking fasteners. In some embodiments, the holes 130a-130f are arranged in series such that no two holes 130a-130f overlap along a width of the shaft portion 110.

In addition, the shaft portion 110 comprises one or more bi-directional dynamic compression slots 132a, 132b interspersed between the holes 130a-130f. The slots 132a, 132b are elongated in length relative to the holes 130a-130f, and are configured to receive one or more non-locking fasteners therein. While the present embodiment illustrates two dynamic compression slots 132a, 132b, in some embodiments, there can be three or more compression slots. In some embodiments, the dynamic compression slots 132a, 132b allow for static insertion of non-locking screws into the shaft portion 110 of the bone. In some embodiments, they also allow for compression (e.g., between 0.5-2 mm, such as 1 mm, of compression) along the shaft portion 110 of the bone through eccentric insertion of a non-locking screw. In some embodiments, the locations of the dynamic compression slots 132a, 132b are optimized for typical intercondylar splits and osteotomies.

In addition to the holes 130a-130f and the compression slots 132a, 132b, the shaft 110 further comprises a kickstand hole 135. In some embodiments, the kickstand hole 135 comprises a polyaxial locking hole for receiving a locking fastener therein. The kickstand hole 135 is advantageously designed to receive a fastener that targets the strong cortical bone in the posteromedial cortex of the condylar region, thereby promoting angular stability. Additionally, the kickstand hole is useful for providing enhanced fixation for comminuted fractures in the metaphyseal region of the bone, due to its oblique angle relative to the upper surface of the plate. In some embodiments, the kickstand hole 135 is angled between 23-33 degrees, or in some embodiments between 27-29 degrees, upwards from a normal plane of the upper surface of the plate.

The shaft portion 110 comprises an anterior side 106 and a posterior side 108 that form the edges of the shaft portion 110. The anterior side 106 and posterior side 108 can include one or more waisted edge scallops 136. Advantageously, the one or more waisted edge scallops 136 permit some bending of the shaft portion 110 without deforming the holes, thereby promoting uniform load transfer. In some embodiments, the shaft portion 110 can have a pre-contoured geometry. Advantageously, the pre-contoured geometry can allow an optimal fit along an entire lateral aspect of a femur. In lengthier versions of the plate 100, there can be an anterior bow and slight shaft twist to mate with proximal femoral anatomy. In addition, in some embodiments, the underside of the bone plate 100 can be arced to mate with the cylindrical nature of the femoral shaft.

The distal end of the shaft portion 110 transitions into the wider, distal portion 104 of the bone plate 100. The distal portion 104 of the bone plate 100 is configured to reside at or near the condylar region of the femur 5. The distal portion 104 comprises holes or openings 140a, 140b, 140c, 140d, 140e, 140f, 140g, 140h that are configured to receive one or more fasteners or screws therein. In some embodiments, the holes 140a-140h comprise polyaxial locking holes that can accommodate screws (e.g., between 3.5-7.5 mm screws, such as 4.5 mm screws). The locking holes may be thread-forming such that a thread is formed within the locking hole as the fastener is inserted therein. In some embodiments, the polyaxial locking holes 140a-140h can have a cone of angulation of up to between 30 to 50 degrees, and more particularly 40 degrees, according to some embodiments. The polyaxial locking holes 140a-140h thus accommodate fasteners of different angles. Advantageously, in some embodiments, the polyaxial locking holes are designed to accommodate multi-planar diverging trajectories to allow a surgeon to select optimal screw trajectories to avoid any existing hardware in the condylar region. In other words, fasteners inserted into the condylar region will avoid other similarly inserted fasteners or other pre-existing hardware that may have been inserted previously in the region. While the present embodiment includes eight polyaxial holes 140a-140h, one skilled in the art will appreciate that the bone plate 100 can include less than eight polyaxial holes or greater than eight polyaxial holes. Furthermore, as the bone plate 100 can include both fixed angle fasteners (e.g., in the shaft 110 of the bone plate 100) and polyaxial fasteners (e.g., in the distal portion 104 of the bone plate 100), the bone plate 100 can be provided relative to an underlying with just enough stiffness to accommodate adequate healing.

In some embodiments, the holes 140a-140h can include one or more holes that are nominally angled so that they are parallel to a knee joint. These holes can receive one or more fasteners or screws that are parallel to the knee joint, thereby helping in proper alignment of the bone plate 100 relative to bone. In the present embodiment, holes 140b, 140d, 140e can be parallel to a knee joint and can be considered to be condylar realignment holes. Advantageously, these condylar realignment holes can help to restore the anatomic alignment of the articular block to prevent *varus*/valgus deformities and post-traumatic arthritis. In other words, holes 140b, 140d, 140e (which are a subset of the polyaxial holes 140a-140h) can help guide one or more fasteners therethrough that are parallel to the knee joint, thereby helping to ensure proper alignment between the bone plate and underlying bone. By providing proper alignment, this advantageously helps to prevent *varus*/valgus deformities and post-traumatic arthritis. One skilled in the art will appreciate that while holes 140b, 140d, 140e can be formed as condylar realignment holes, other holes in the distal end can also be used for similar purposes.

In addition to the holes 140a-140h, the distal portion 104 of the plate 100 further comprises a distal pair of k-wire holes 142. Like the proximal k-wire hole 122, the k-wire holes 142 allow temporary fixation of the bone plate 100 to bone with k-wires.

In addition to the holes 140a-140h and k-wire holes 142, the distal portion 104 of the plate 100 further comprises three indentations 144. In some embodiments, the indentations 144 are rounded or spherical. The purpose of the indentations 144 is to help accommodate a portion of an instrument (e.g., an attachment post of an associated aiming instrument). The instrument can be used to accurately guide fasteners or screws into respective holes in the bone plate 100. The instrument can rest against one or more of the indentations 144, thereby ensuring proper alignment and orientation between the instrument and the plate 100. Unlike the holes 140a-140h and k-wire holes 142, the indentions 144 do not extend through the upper surface to the lower surface of the bone plate 100. Rather, they are formed partially along the height of the bone plate 100.

The distal portion 104 of the plate 100 can have a distinct contour. In particular, the distal portion 104 of the plate 100 can comprise a concave cutout or lag screw groove 148. Screws or fasteners can sometimes be placed externally to the bone plate 100 to lag fragments of the articular block prior to plate placement. The lag screw groove 148 advantageously accommodates and/or permits placement of these external lag/compression screws.

In some embodiments, the distal portion 104 of the plate 100 further comprises a variable chamfered surface 149. The variable chamfered surface 149 advantageously has different amounts of material removed from a top surface of the bone plate 100 at the distal end, thereby permitting a thinner surface in an area where soft tissue cover is minimal. This desirably helps to prevent irritation around the knee region.

In some embodiments, the distal portion 104 of the bone plate 100 further comprises an anterior side and a posterior side, wherein the posterior side has a raised contour relative to the anterior side in a vertical direction along the height of the bone plate 100. As shown in FIG. 3, the bone plate 100 comprises a raised posterior side 146 that can be between 2-10 mm higher than an anterior side. In some embodiments, the raised posterior side 146 has an underside that is between 2-10 mm higher than an underside of an opposing anterior side of the bone plate 100. The purpose of the raised posterior side 146 is that it advantageously accommodates an anatomical ridge on the posterior side of the femoral condyle known as the epicondyle. The raised posterior side 146 is advantageously designed to reside or sit on the epicondyle, thereby providing a mechanism by which a surgeon can key the bone plate 100 into place on the condylar surface. Furthermore, the raised posterior side 146 helps to stabilize the bone plate 100 over a bone, which would likely be unsteady without the raised feature. In addition to the raised contour, the bone plate 100 also includes condylar contouring around its distal perimeter to mimic the metaphyseal and epiphyseal anatomy to guide plate placement.

In some embodiments, the overall height or thickness of the bone plate 100 can be variable along its length. In some embodiments, the height or thickness of the bone plate 100 can be greater in the shaft 110 than in the distal portion 104. In some embodiments, the thickness in the shaft 110 can be between 3.0-6.0 mm, while the thickness in the distal portion 104 can be between 1.5-4.5 mm. The variable thickness advantageously provides ideal stiffness to the bone plate 100, while also balancing the need to be careful around surrounding tissue around the bone plate. For example, a less thick distal portion 104 can help reduce unnecessary contact with adjacent tissue, thereby reducing irritation around a knee region.

FIG. 4 is a top perspective view of a broad bone plate in accordance with some embodiments of the present application. The broad bone plate 200 includes many similar features as the narrower bone plate 100, but is wider than the narrower bone plate 100. In some embodiments, a distal portion 204 of the bone plate 200 can be between 7-11 mm, or approximately 9 mm, wider than the narrower bone plate 100. This additional width permits space for additional (e.g., two or more) polyaxial locking holes 240, as well as one or more k-wire holes 242. In some embodiments, a shaft portion 210 of the bone plate 200 can be between 5.5-9.5 mm, or approximately 7.5 mm, wider than the narrower bone plate 100. This additional width permits space for additional fixed angle, stacked locking holes 230. In some embodiments, the additional width of the shaft 210 provides space for two, three or more locking holes 230 along its width.

The bone plate 200 comprises a proximal portion 202 and a distal portion 204. In between the proximal portion 202 and distal portion 204 is a shaft 210 having an anterior sidewall 206 and a posterior sidewall 208. Along the length of the bone plate 200 are a series of holes or openings for receiving screws or fasteners therein.

The proximal portion 202 of the bone plate 200 comprises a tapered tip 220. In some embodiments, the tapered tip 220 serves as the lead portion of the bone plate 200 to enter into an incision. In some embodiments, the tapered tip 220 allows for simplified submuscular plate insertion to minimize incision length. The proximal portion 202 further comprises a k-wire hole 222 for receiving a k-wire therein to guide bone plate 200 to a desired surgical site. The k-wire hole 222 allows for temporary fixation of the bone plate 200 to bone via a k-wire. In some embodiments, the k-wire hole 222 is unthreaded. In addition, the proximal portion 202 further comprises an articulated tensioning device (ATD) slot 224. The ATD slot 224 is configured to receive a portion of a tension or compression device (not shown) that can help to bring bone fragments together for healing. In some embodiments, the ATD slot 224 is composed of a through hole and a cylindrical shaped undercut on the bottom of the plate 200.

The proximal portion 202 transitions into the shaft portion 210. The shaft portion 210 comprises multiple holes or openings 230a, 230b, 230c, 230d, 230e, 230f, 230g, 230h, 230i, 230j that are configured to receive fasteners therein. In some embodiments, holes 230a-230j are configured to be fixed angle, stacked locking holes that can accommodate screws (e.g., between 3.5-7.5 mm screws, such as 4.5 mm screws). The fixed angle, stacked locking holes advantageously allow for mono-axial insertion of fasteners that lock to the bone plate 200. In some embodiments, these holes can also accommodate non-locking fasteners. In some embodiments, the holes 230a-230j are distributed such that no two holes 230a-230j overlap along a width of the shaft portion 110. However, one skilled in the art will appreciate that the shaft portion 210 is wide enough to accommodate two or more holes 230a-230j side-by-side. In the present embodiment, the shaft includes distinct groups of three holes 230a-230j side-by-side along the entire length of the plate.

In addition, the shaft portion 210 comprises one or more bi-directional dynamic compression slots 232a, 232b interspersed between the holes 230a-230j. The slots 232a, 232b are elongated in length relative to the holes 230a-230j, and are configured to receive one or more non-locking fasteners therein. While the present embodiment illustrates two dynamic compression slots 232a, 232b, in some embodiments, there can be three or more compression slots. In some embodiments, the dynamic compression slots 232a, 232b allow for static insertion of non-locking screws into the shaft portion 210 of the bone. In some embodiments, they also allow for compression (e.g., between 0.5-2 mm, such as 1 mm, of compression) along the shaft portion 210 of the bone through eccentric insertion of a non-locking screw. In some embodiments, the locations of the dynamic compression slots 232a, 232b are optimized for typical intercondylar splits and osteotomies. In the present embodiments, each of the dynamic compression slots 232a, 232b is positioned adjacent to a pair of locking holes 230.

In addition to the holes 230a-230f and the compression slots 232a, 232b, the shaft 210 further comprises a kickstand hole 235. In some embodiments, the kickstand hole 235 comprises a polyaxial locking hole for receiving a locking fastener therein. The kickstand hole 235 is advantageously designed to receive a fastener that targets the strong cortical bone in the posteromedial cortex of the condylar region, thereby promoting angular stability. Additionally, the kickstand hole is useful for providing enhanced fixation for comminuted fractures in the metaphyseal region of the bone, due to its oblique angle relative to the upper surface of the plate.

The shaft portion 210 comprises an anterior side 206 and a posterior side 208 that form the edges of the shaft portion 210. The anterior side 206 and posterior side 208 can include one or more waisted edge scallops 236. Advantageously, the one or more waisted edge scallops 236 permit some bending of the shaft portion 210 without deforming the holes, thereby promoting uniform load transfer. The waisted edge scallops 236 are slightly larger than the waisted edge scallops 136 to take into account the wider shaft. In some embodiments, the shaft portion 210 can have a pre-contoured geometry. Advantageously, the pre-contoured geometry can allow an optimal fit along an entire lateral aspect of a femur. In lengthier versions of the plate 200, there can be an anterior bow and slight shaft twist to mate with proximal femoral anatomy. In addition, in some embodiments, the underside of the bone plate 200 can be arced to mate with the cylindrical nature of the femoral shaft.

The distal end of the shaft portion 210 transitions into the wider, distal portion 204 of the bone plate 200. The distal portion 204 of the bone plate 200 is configured to reside at or near the condylar region of the femur 5. The distal portion 204 comprises holes or openings 240a, 240b, 240c, 240d, 240e, 240f, 240g, 240h, 240i, 240j that are configured to receive one or more fasteners or screws therein. In some embodiments, the holes 240a-240j comprise polyaxial locking holes that can accommodate screws (e.g., between 3.5-7.5 mm screws, such as 4.5 mm screws). In some embodiments, the polyaxial locking holes 240a-240j can have a cone of angulation of up to between 30 to 50 degrees, and more particularly 40 degrees, according to some embodiments. The polyaxial locking holes 240a-240j thus accommodate fasteners of different angles. Advantageously, in some embodiments, the polyaxial locking holes are designed to accommodate several multi-planar diverging trajectories to allow a surgeon to select optimal screw trajectories to avoid any existing hardware in the condylar region. In other words, fasteners inserted into the condylar region will avoid other similarly inserted fasteners or other pre-existing hardware that may have been inserted previously in the region. While the present embodiment includes ten polyaxial holes 240a-240j, one skilled in the art will appreciate that the bone plate 200 can include less than ten polyaxial holes or greater than ten polyaxial holes. Furthermore, as the bone plate 200 can include both fixed angle fasteners (e.g., in the shaft 210 of the bone plate 200) and polyaxial fasteners (e.g., in the distal portion 204 of the bone plate 200), the bone plate 200 can be provided relative to an underlying with just enough stiffness to accommodate adequate healing.

In some embodiments, the holes 240a-240j can include one or more holes that are nominally angled so that they are parallel to a knee joint. These holes can receive one or more fasteners or screws that are parallel to the knee joint, thereby helping in proper alignment of the bone plate 200 relative to bone. In the present embodiment, holes 240b, 240e, 240f can be parallel to a knee joint and can be considered to be condylar realignment holes. Advantageously, these condylar realignment holes can help to restore the anatomic alignment of the articular block to prevent *varus*/valgus deformities and post-traumatic arthritis. In other words, holes 240b, 240e, 240f (which are a subset of the polyaxial holes 240a-240j) can help guide one or more fasteners therethrough that are parallel to the knee joint, thereby helping to ensure proper alignment between the bone plate and underlying bone. By providing proper alignment, this advantageously helps to prevent *varus*/valgus deformities and post-traumatic arthritis. One skilled in the art will appreciate that while holes 240b, 240e, 240f are considered condylar realignment holes, these are only representative, and other holes in the distal portion can also be considered condylar realignment holes.

In addition to the holes 240a-240j, the distal portion 204 of the plate 200 further comprises a distal pair of k-wire holes 242. Like the proximal k-wire hole 222, the k-wire holes 242 allow temporary fixation of the bone plate 200 to bone with k-wires.

In addition to the holes 240a-240j and k-wire holes 242, the distal portion 204 of the plate 200 further comprises three indentations 244. In some embodiments, the indentations 244 are rounded or spherical. The purpose of the indentations 244 is to help accommodate a portion of an instrument (e.g., an attachment post of an associated aiming instrument). The instrument can be used to accurately guide fasteners or screws into respective holes in the bone plate 200. The instrument can rest against one or more of the indentations 244, thereby ensuring proper alignment and orientation between the instrument and the plate 200. Unlike the holes 240a-240j and k-wire holes 242, the indentations 244 do not extend through the upper surface to the lower surface of the bone plate 200. Rather, they are formed partially along the height of the bone plate 200.

In some embodiments, the distal portion 204 of the plate 200 further comprises a variable chamfered surface 249. The variable chamfered surface 249 advantageously has different amounts of material removed from a top surface of the bone plate 200 at the distal end, thereby permitting a thinner surface in an area where soft tissue cover is minimal. This desirably helps to prevent irritation around the knee region.

In some embodiments, the distal portion 204 of the bone plate 200 further comprises an anterior side and a posterior side, wherein the posterior side has a raised contour relative to the anterior side. As shown in FIG. 4, the bone plate 200 comprises a raised posterior side 246 that can be between 2-10 mm higher than an anterior side. In some embodiments, the raised posterior side 246 has an underside that is between 2-10 mm higher than an underside of an opposing anterior side of the bone plate 200. The purpose of the raised posterior side 246 is that it advantageously accommodates an anatomical ridge on the posterior side of the femoral condyle known as the epicondyle. The raised posterior side 246 is advantageously designed to reside or sit on the epicondyle, thereby providing a mechanism by which a surgeon can key the bone plate 200 into place on the condylar surface. Furthermore, the raised posterior side 246 helps to stabilize the bone plate 200 over a bone, which would likely be unsteady without the raised feature. In addition to the raised contour, the bone plate 200 also includes condylar contouring around its distal perimeter to mimic the metaphyseal and epiphyseal anatomy to guide plate placement.

Figure 5:
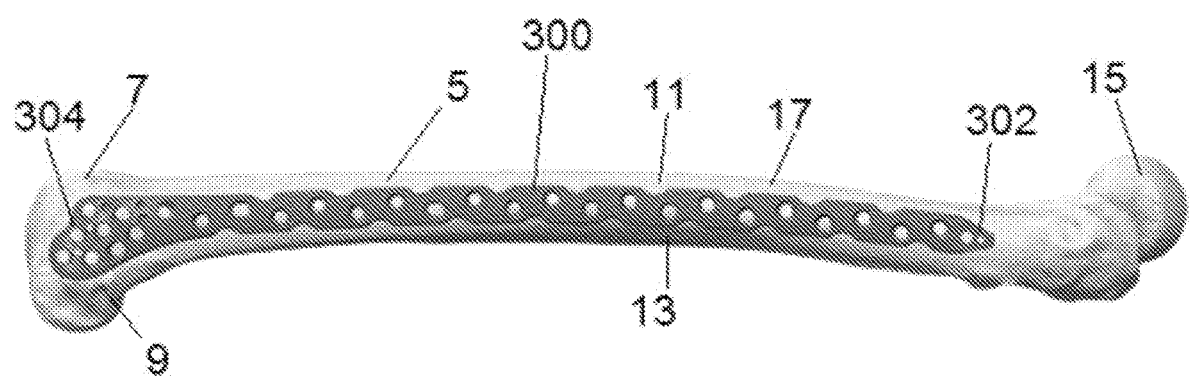
FIG. 5 is a view of an alternative bone plate on bone in accordance with some embodiments of the present application.

FIG. 5 is a view of an alternative bone plate on bone in accordance with some embodiments of the present application. The bone plate 300 comprises a plate that is lengthier than the bone plates 100, 200 in prior embodiments. The bone plate 300 is designed to extend along a majority of the length of a femur 5. In some embodiments, as shown in FIG. 5, the bone plate 300 extends from the distal condylar region 7 close to the proximal region 15 of the bone plate 300. By spanning the extending length, the bone plate 300 may help heal and prevent fractures that are higher up the femur and near the proximal region 15. Additionally, a lengthier bone plate can assist in providing a longer working length, which helps to modulate the stiffness of the plate and screw construct to promote faster healing.

FIG. 6 is a top view of a lengthened, narrow bone plate in accordance with some embodiments of the present application. While the bone plate 300 has a number of similar features to bone plates 100, 200, the bone plate 300 is much longer. In some embodiments, the bone plate 300 has a length of between 400 and 500 mm, such as approximately 460 mm.

The bone plate 300 can include three distinct regions, identified by the perforated lines. These regions include a proximal region 302, a medial region 306 and a distal region 304.

The proximal region 302 comprises a tapered distal end that includes a tapered tip 320, k-wire hole 322 and ATD slot 324. In addition, the proximal region 302 comprises a series of proximal holes 328. In some embodiments, these proximal holes 328 are polyaxial and nominally angled toward the outer edge of the bone plate 300 in order to assist in dodging a hip stem in the proximal femur. While the present embodiment shows ten proximal holes 328, in other embodiments, the proximal region 302 includes less than ten or greater than ten proximal holes 328. In addition, while the present embodiment shows ten proximal holes 328 that are similar to one another (e.g., polyaxial), in some embodiments, the proximal holes 328 can be a combination of monoaxial and polyaxial locking holes, or just monoaxial holes.

The medial region 306 comprises a shaft region having a series of holes or openings for receiving fasteners or screws therein. As shown in FIG. 6, some of the holes can be stacked holes 330 that can accept locking or non-locking screws, while some of the holes can be elongated dynamic compression slots 332 that can accept non-locking screws. In the present embodiments, the medial region 306 comprises twelve stacked holes 330 and two dynamic compression slots 332. However, one skilled in the art will appreciate that in some embodiments, the medial region 306 can include less than or greater than twelve stacked holes 330 and two dynamic compression slots 332.

The distal region 304 of the bone plate 300 comprises a flared out, wider region that resides on a condylar region of bone. In some embodiments, the distal region 304 includes a pair of distal k-wire holes 342 for receiving guiding k-wires therein. The distal region 304 further includes three indentations 344 that are configured to engage a portion of an instrument (e.g., an alignment post of an aiming guide). The distal region 304 further includes a series of holes or openings for receiving one or more fasteners or screws therein. These include one kickstand hole 335 and eight polyaxial locking holes 340, which are advantageously designed such that fasteners that are inserted therethrough do not interfere with one another. In addition to these features, the distal region 304 can further include a lag screw groove 348 and a raised posterior side 346 that can accommodate an epicondylar flare.

As shown in FIG. 6, the bone plate 300 comprises different types of holes in the three distinct regions—proximal region 302, medial region 306 and distal region 304. In some embodiments, the distal region 304, which encompasses the condylar region, comprises polyaxial locking holes 328. In the medial region 306, the polyaxial locking holes 328 can transition into non-polyaxial or fixed holes 330. In some embodiments, the fixed holes 330 can be stacked holes. In the proximal region 302, the fixed holes 330 can transition into polyaxial locking holes 340.

FIG. 7 is a top view of a lengthened, broad bone plate in accordance with some embodiments of the present application. Like the bone plate 300, bone plate 400 has a number of similar features to bone plates 100, 200, but is much longer. In some embodiments, the bone plate 400 has a length of between 400 and 500 mm, such as approximately 460 mm. The bone plate 400 is also wider than the bone plate 300, thereby accommodating a number of distinct hole patterns along its length.

The bone plate 400 can include three distinct regions, identified by the perforated lines. These regions include a proximal region 402, a medial region 406 and a distal region 404. All three regions (402, 404, and 406) can contain groups of two or more holes side-by-side along the length of the plate. In the present embodiments, the shaft includes distinct groups of three holes side-by-side along the entire length of the plate.

The proximal region 402 comprises a tapered distal end that includes a k-wire hole 422 and ATD slot 424. In addition, the proximal region 402 comprises a series of proximal holes. In some embodiments, these proximal holes comprise polyaxial locking holes 428 that are nominally angled toward the outer edge of the bone plate 400 in order to assist in dodging a hip stem in the proximal femur. In between pairs of polyaxial locking holes 428 are stacked holes 426. In some embodiments, both the polyaxial locking holes 428 and stacked holes 426 can receive locking or non-locking fasteners. In the present embodiment, the proximal region 402 comprises five sets of holes, whereby each set comprises a pair of polyaxial locking holes 428 and a stacked hole 426.

The medial region 406 comprises a shaft region having a series of holes or openings for receiving fasteners or screws therein. As shown in FIG. 7, some of the holes can be stacked holes 430 that can accept locking or non-locking screws, while some of the holes can be elongated dynamic compression slots 432 that can accept non-locking screws. In the present embodiments, the medial region 406 comprises seven sets of holes, whereby each set comprises two or more stacked holes 430. In some of the sets, at least one dynamic compression slot 432 is provided between the two or more stacked holes.

The distal region 404 of the bone plate 400 comprises a flared out, wider region that resides on a condylar region of bone. In some embodiments, the distal region 404 includes a pair of distal k-wire holes 442 for receiving guiding k-wires therein. The distal region 404 further includes three indentations 444 that are configured to engage a portion of an instrument (e.g., an alignment post of an aiming guide). The distal region 404 further includes a series of holes or openings for receiving one or more fasteners or screws therein. These include one kickstand hole 435 and ten polyaxial locking holes 440, which are advantageously designed such that fasteners that are inserted therethrough do not interfere with one another. In addition to these features, the distal region 404 can further include a raised posterior side 446 that can accommodate an epicondylar flare.

Figure 8:
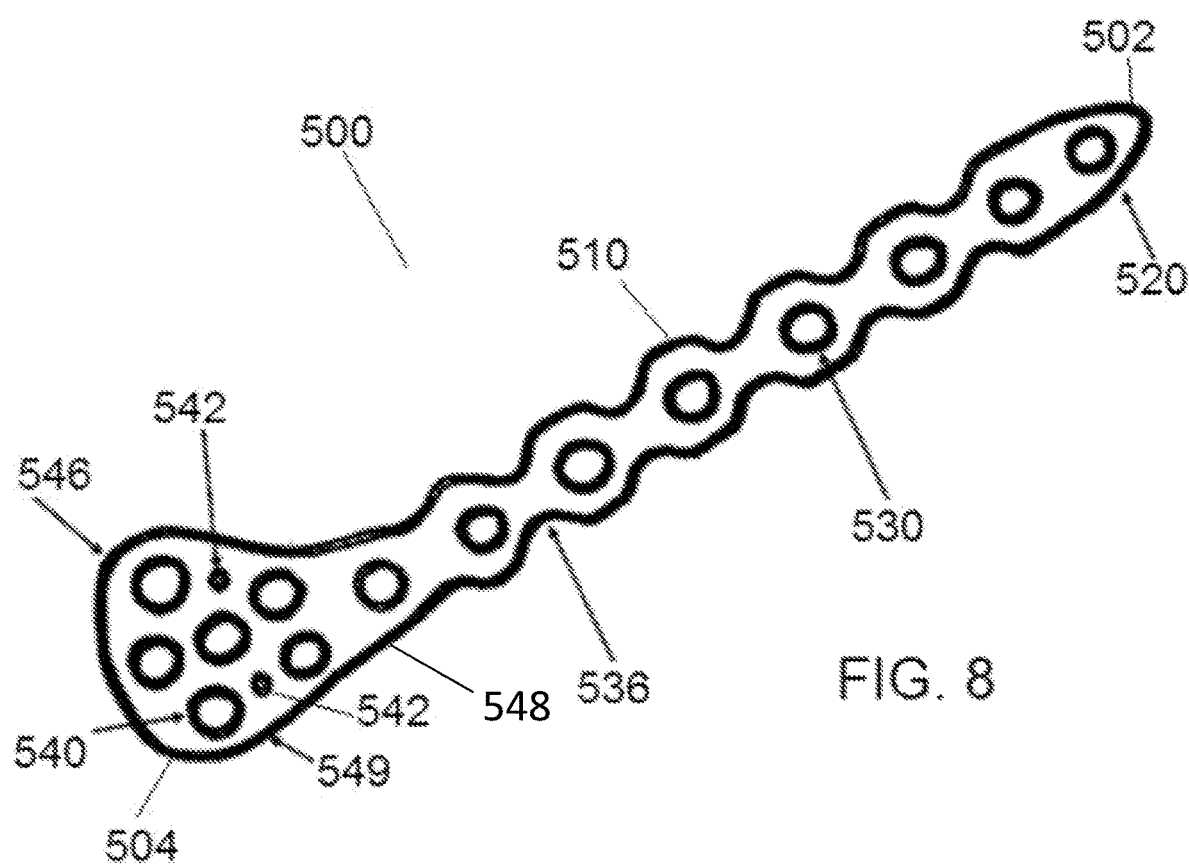
FIG. 8 is a top view of a medial plate in accordance with some embodiments of the present application.

FIG. 8 is a top view of a medial plate in accordance with some embodiments of the present application. The medial plate 500 is inserted through an incision over the anteromedial of the distal femur or an S-shaped incision on the posterior side of the knee joint. The medial plate 500 includes similar features as the narrow and broad locking plates 100, 200. In some embodiments, the longest length of the medial plate will sit no less than 8 cm below the lesser trochanter in order to preserve the vessels and nerve pathways on the medial side of the femur. In some embodiments, the thickness of the plate 500 varies along a length of the plate 500. For example, the plate 500 can be thicker in a proximal region (e.g., between 2.0-4.0 mm, such as approximately 3.0 mm) than in a distal region (e.g., between 1.5-3.0 mm, such as approximately 2.25 mm).

The medial plate 500 comprises a proximal portion 502 and a distal portion 504 and a shaft 510 therebetween 510. The proximal portion 502 comprises a tapered insertion tip 520. Along the proximal portion 502 and shaft 510 are a series of holes 530 for receiving fasteners therein. In some embodiments, the holes 520 are polyaxial locking holes. In other embodiments, the holes 520 are fixed angled stacked locking holes. In some embodiments, the holes 520 are a combination of polyaxial locking holes or fixed angle stacked locking holes. In some embodiments, the holes 520 accommodate screws of various sizes, such as between 3.5-7.5 mm screws, such as approximately 4.5 mm. The shaft 510 further includes waisted edge scallops 536.

The distal portion 504 of the medial plate 500 comprises similar features as in prior embodiments, including a pair of distal k-wire holes 542 and six polyaxial locking holes 540. The polyaxial locking holes 540 can accommodate fasteners or screws that are between 3.0 and 6.0 mm, or approximately 4.5 mm. Furthermore, the distal portion 504 comprises a raised posterior side 546 to accommodate an epicondylar flare, as well as condylar contouring 506 to accommodate distinct anatomy. In some embodiments, the distal portion 504 also comprises a variable chamfered surface 549.

Figure 9:
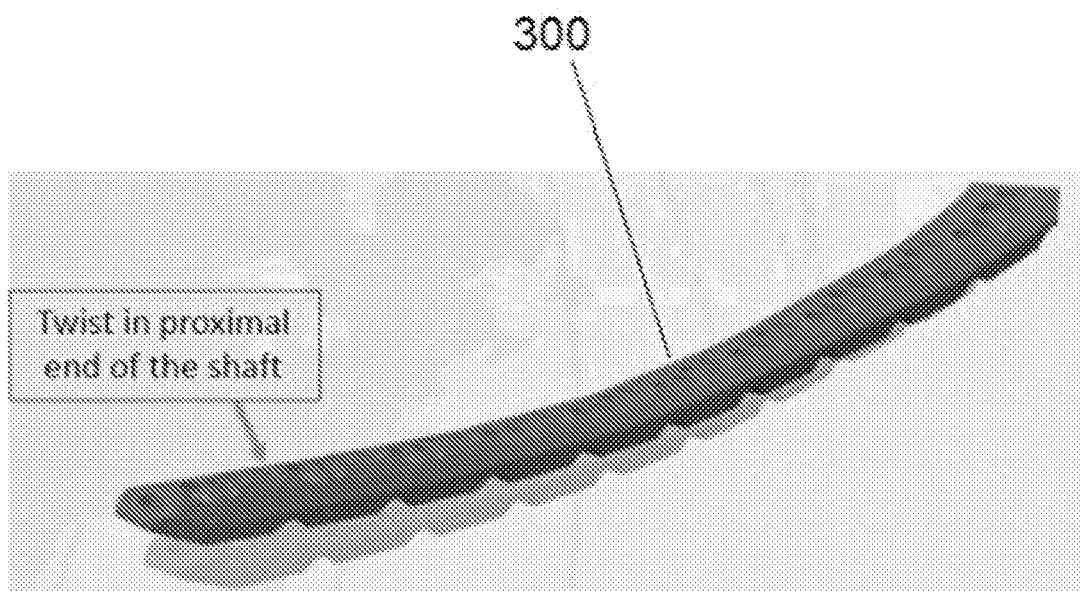
FIG. 9 is a top perspective view of a representative plate including a twist up its shaft.

FIG. 9 is a top perspective view of a representative plate including a twist up its shaft. From this view, one can see how the proximal portion of the representative shaft 300 can have an upward twist from a more medial section of the plate. The advantage of the upward twist is that the plate is a better anatomical fit with bone.

FIG. 10 is a cross-sectional view of a section of a representative plate showing an arced contour of an underside. FIG. 11 is a cross-sectional view of a different section of a representative plate showing an arced contour of an underside. From these views, one can see how the arced surface varies in radius and centrality along the length of the plate. For example, the underside in FIG. 10 has a radius of R1, while the underside in FIG. 11 has a radius of R2, wherein R1 is different from R2. By having different arced contours along different sections of the plate, this also helps to give the plate a better anatomical fit to bone. In some embodiments, R1 and R2 can have a dimension between about 25 mm to 250 mm, whereby R1 is different from R2.

Figure 12:
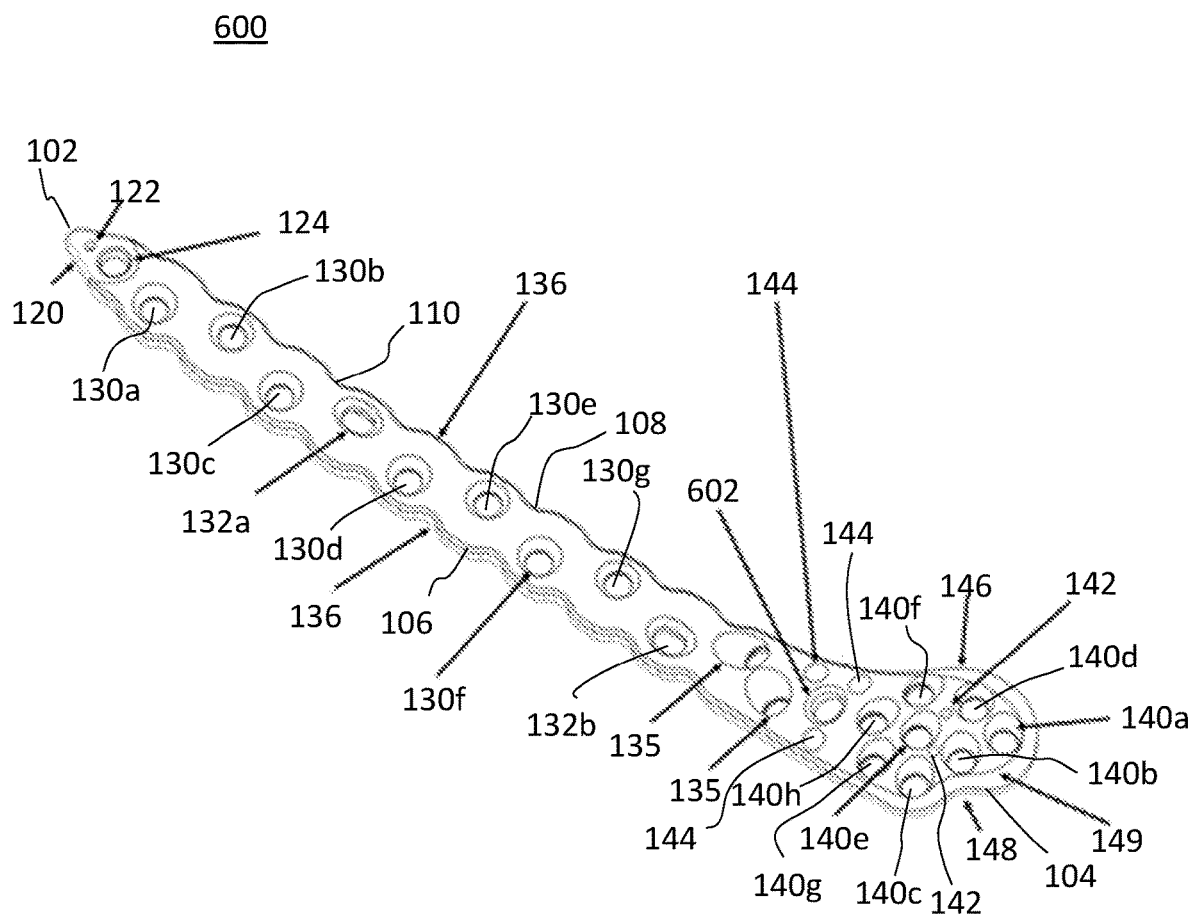
FIG. 12 is a top perspective view of another embodiment of a narrow bone plate.

Turning now to FIG. 12, a top perspective view of a narrow bone plate 600 according to yet another embodiment is shown. The narrow bone plate 600 is similar to narrow bone plate 100 shown in FIG. 3 and like elements are labeled the same. Similar to plate 100, bone plate 600 comprises proximal portion 102 and distal portion 104 with shaft 110 extending therebetween having anterior sidewall 106 and posterior sidewall 108.

Similar to holes or openings 130a-130f in plate 100, plate 600 includes a plurality of holes or openings 130a-130g that are configured to receive fasteners therein. In some embodiments, holes 130a-130g may be configured as locking holes, which may be able to accept locking or non-locking screws. The openings 130a-130g may be in the form of 4.5 mm polyaxial locking holes. The openings 130a-130g may be staggered to prevent new linear fracture lines in the metaphyseal and diaphyseal regions.

Similar to plate 100, the shaft portion 110 of plate 600 comprises one or more bi-directional dynamic compression slots 132a, 132b. These slots 132a, 132b may be configured to receive one or more non-locking fasteners therein and may allow for compression along the shaft portion 110 of the bone. The bi-directional dynamic compression slots 132a, 132b may allow for static insertion of non-locking screws into the shaft of the bone and/or may allow for 1 mm of compression along the shaft of the bone through eccentric insertion of a non-locking screw. The locations of the dynamic compression slots 132a, 132b were optimized for typical intercondylar splits and osteotomies.

The articulated tensioning device (ATD) hole 124 is composed of a through hole in the tip of the plate 600 and a cylindrical shaped undercut on the bottom surface of the plate 600. The hole mates with an ATD and allows for compression or tensioning of fracture fragments.

Plate 600 further includes a plurality of kickstand holes 135. For example, in this embodiment, the shaft portion 110 may include two kickstand holes 135 separated from one another and oriented in different directions. The kickstand holes 135 may each comprise a polyaxial locking hole for receiving a locking fastener therein. In the metaphyseal region of the lateral plates, the two kickstand strut screws permit fixation in the anteromedial and posteromedial cortices of the medial femoral condyle in the lateral plates. The screw targets the strong cortical bone of the posteromedial cortex in order to enhance screw fixation, prevent pull-out, and promote angular stability via triangular fixation.

The anterior side 106 and posterior side 108 can include one or more waisted edge scallops 136. Advantageously, the one or more waisted edge scallops 136 permit some bending of the shaft portion 110 without deforming the holes, thereby promoting uniform load transfer.

The distal end of the shaft portion 110 transitions into the wider, distal portion 104 of the bone plate 600. Similar to plate 100, plate 600 includes holes or openings 140a-140h that are configured to receive one or more fasteners or screws therein, including locking or non-locking screws. The holes 140a-140h may comprise polyaxial locking holes, for example, with a cone of angulation. The cluster of holes 140a-140h may be nominally targeted in several multi-planar diverging trajectories to allow the surgeon to select optimal screw trajectories to avoid any existing hardware in the condyle.

The distal portion 104 of the plate 600 may further comprises a distal pair of k-wire holes 142. Like the proximal k-wire hole 122, the k-wire holes 142 allow temporary fixation of the bone plate 600 to bone with k-wires.

The distal portion 104 of the plate 600 may include three indentations 144, for example, or blind openings being rounded or spherical, to help accommodate a portion of an instrument (e.g., an attachment post of an associated aiming instrument).

In this embodiment, plate 600 further includes a dedicated aiming arm attachment hole 602. The dedicated aiming arm attachment hole 602 may be a threaded hole, for example, for attaching the attachment post of an associated aiming instrumentation for the system.

The thickness of the plate 600 may vary from about 4.5 mm proximally to 3.6 mm distally, varying through the metaphyseal and epiphyseal regions. The transition in thickness may begin about 129 mm from the most distal edge of the plate 600. The width of the plate 600 may vary from about 33 mm wide in the head of the plate 600 to about 17.5 mm wide in the shaft of the plate 600. The transition in width may also begin about 129 mm from the most distal edge of the plate 600.

Figure 13:
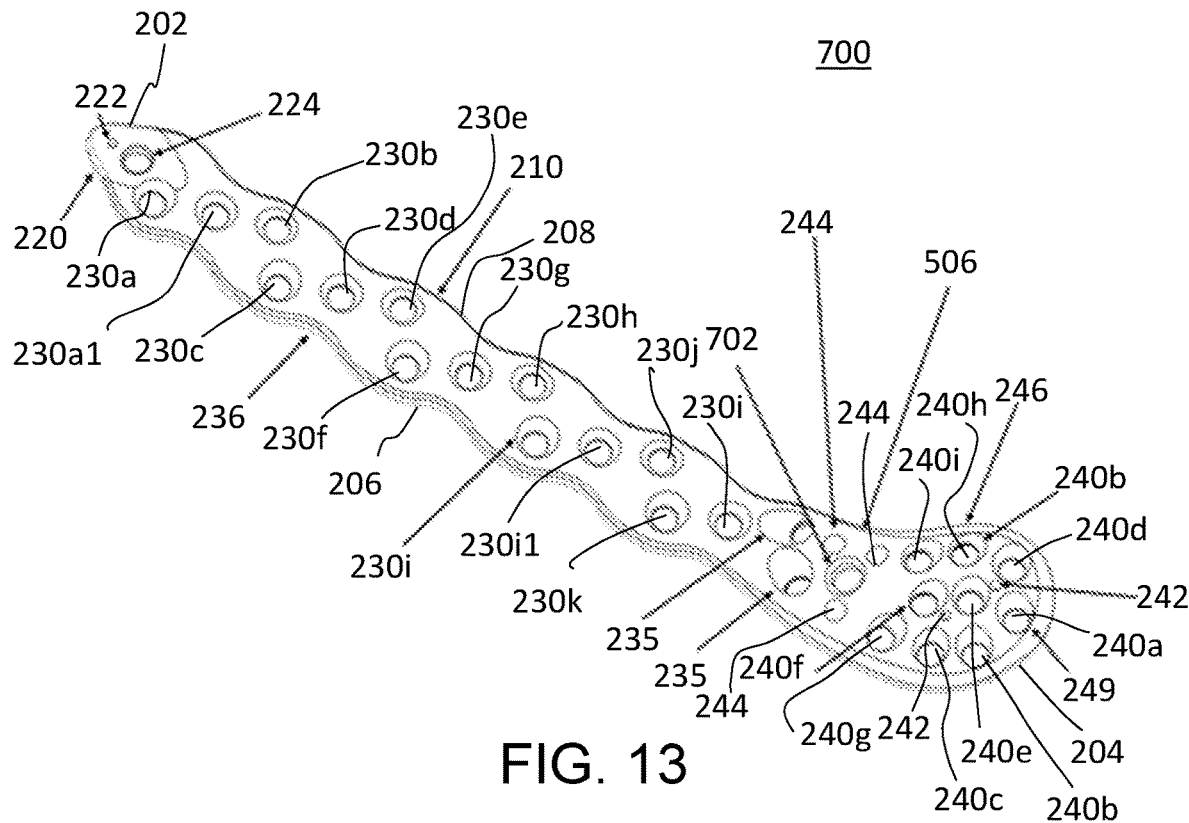
FIG. 13 is a top perspective view of another embodiment of a broad bone plate.
Figure 14:
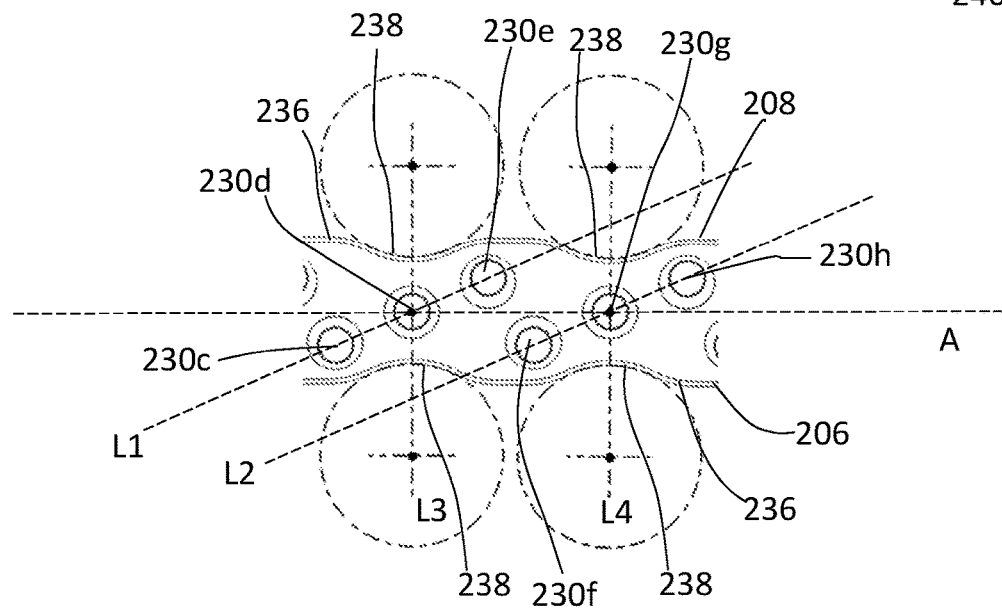
FIG. 14 is a close-up view of the geometry of the broad bone plate of FIG. 13.

Turning now to FIGS. 13 and 14, a broad lateral bone plate 700 according to yet another embodiment is shown. The broad lateral bone plate 700 is similar to broad bone plate 200 shown in FIG. 4 and like elements are labeled the same. Similar to plate 200, bone plate 700 comprises proximal portion 202 and distal portion 204 with shaft 210 extending therebetween having anterior sidewall 206 and posterior sidewall 208. The broad lateral locking plate 700 may be inserted through an incision over the lateral aspect of the distal femur and may provide some of the same types of features as the narrow version 600.

The shaft portion 210 comprises a plurality of holes or openings 230a, 230a1, 230b, 230c, 230d, 230e, 230f, 230g, 230h, 230i, 230i1, 230j, 230k, 230l that are configured to receive fasteners therein. As compared to plate 200, plate 700 replaces dynamic compression slots 232a, 232b with openings 230a1 and 230i1 and additional openings 230K and 230l are added. The plurality of openings 230a-230l may be 4.5 mm polyaxial locking holes in the distal cluster that may be nominally targeted in several multi-planar diverging trajectories to allow the surgeon to select optimal screw trajectories to avoid any existing hardware in the condyle. The plurality of openings 230a-230l may accept locking or non-locking screws. The plurality of openings 230a-230l in the shaft 210 of the plate 700 may be staggered to prevent new linear fracture lines in the metaphyseal and diaphyseal regions. In particular, the plurality of openings 230a-230l may be a repeating pattern of three holes (e.g., 230a, 230a1, 230b).

As best seen in FIG. 14, a first virtual line segment L1 connecting a repeating pattern of three holes (e.g., 230c-230e) through their respective center points may be angled relative to the longitudinal axis A of the plate 700. Similarly, a second virtual line segment L2 connecting a repeating pattern of three holes (e.g., 230f-230h) through their respective center points may be angled relative to the longitudinal axis A of the plate 700. Although two virtual line segments L1, L2 are shown it is evident that the same repeating pattern of three holes repeats along the length of the plate 700. Each line segment L1, L2 connecting a repeating pattern of three holes through their respective center points may be generally aligned substantially parallel to one another.

The center point of the center hole 230d, 230g of each repeating pattern may be aligned generally along the longitudinal axis A of the plate 700. In addition, indentations 238 of the scallop 236 along the anterior and posterior sidewalls 206, 208 may be generally aligned with the center hole 230d, 230g of each repeating pattern. As best seen in FIG. 14, the center of the scallops 236 on both of the side surfaces 206, 208 are aligned with the center of the middle row of shaft holes. The indentations 238 of the scallop 236 along the side surfaces 206, 208 lie on an axis which is perpendicular to the centered longitudinal axis A along the length of the shaft 210. In particular, a virtual line segment L3 connecting a center point for the radius of a first indentation 238 on anterior sidewall 206 to a center point for the radius of a second indentation 238 on the posterior sidewall 208 are generally aligned with the center of the center hole 230d. Similarly, a virtual line segment L4 connecting a center point for the radius of a third indentation 238 on anterior sidewall 206 to a center point for the radius of a fourth indentation 238 on the posterior sidewall 208 are generally aligned with the center of the center hole 230g. It will again be appreciated that although two virtual line segments L3, L4 are shown it is evident that the same repeating pattern of three holes repeats along the length of the plate 700. The undulating scallops 236 result in a shaft profile which continually varies in overall width.

Plate 700 further includes a plurality of kickstand holes 235. For example, in this embodiment, the shaft portion 210 may include two kickstand holes 235 separated from one another and oriented in different directions. The kickstand holes 235 may each comprise a polyaxial locking hole for receiving a locking fastener therein. The polyaxial locking kickstand strut holes 235 are designed to target the strong cortical bone in the anteromedial and posteromedial cortices of the medial condyle and promote angular stability.

Similar to plate 600, plate 700 includes a dedicated aiming arm attachment hole 702 and a plurality of indentations 244 surrounding the attachment hole 702. The dedicated aiming arm attachment hole 702 may be a threaded hole, for example, for attaching the attachment post of an associated aiming instrumentation for the system. As shown, the three indentations 244 or blind openings may be rounded or spherical, to help accommodate a portion of an instrument (e.g., an attachment post of an associated aiming instrument).

The distal portion 204 of the bone plate 700, configured to reside at or near the condylar region of the femur 5, may include a plurality of holes or openings 240a, 240b, 240c, 240d, 240e, 240f, 240g, 240h, 240i, such as polyaxial locking holes, that are configured to receive one or more fasteners or screws therein. This is substantially similar to plate 200 except hole 240j is omitted. One or more k-wire holes 242 may also be positioned in the distal portion 204 of the plate 700.

The thickness of the plate 700 may vary from about 4.5 mm proximally to about 3.6 mm distally varying through the metaphyseal and epiphyseal regions. Like the narrow plate 600, the transition in thickness may begin about 129 mm from the most distal edge of the plate. The width of the plate may vary from about 39 mm wide in the head of the plate 700 to about 24 mm wide in the shaft 210 of the plate 700. The transition in width also begins about 129 mm from the most distal edge of the plate 700.

The main differentiating qualities between the broad plate 700 and the narrow plate 600 are the overall size of the plates and the total number of each type of feature. The distal portion of the plate 700 is about 6 mm wider than that of the narrow plate 600, thereby permitting space for one additional 4.5 mm polyaxial locking hole resulting in a total of 9 polyaxial holes in the distal cluster. As this plate 700 is designed to fill the majority of the lateral femoral condyle and/or abut against the femoral component of a total knee arthroplasty, the lag screw groove is eliminated in the broad plate 700.

The shaft 210 of the broad plate 700 is about 6.5 mm wider than that of the narrow plate 600. With more space, the alternating pattern of polyaxial locking holes in the shaft is increased from 2-wide to 3-wide. Additionally, the waisted edge scallops 236 are slightly larger to take into account the wider shaft 210.

FIGS. 15 and 16 show the longest lengths for each of the two lateral plates 800, 900. These plates 800, 900 are substantially the same as those shown in FIGS. 6 and 7, respectively, and like elements are labeled the same. In these embodiments, the plates 800, 900 further include an additional kickstand opening, 335, 435, respectively, and the associated indentations or blind openings 144, 244, respectively, to help accommodate a portion of an instrument (e.g., an attachment post of the associated aiming instrument). The total length of these plates 800, 900 is about 458 mm and the radius of curvature (i.e. anterior bow) is about 1200 mm. Plate lengths decrease by approximately 31-33 mm, resulting in 11 lengths of each lateral plate and a shortest length of about 137 mm.

The pattern of staggered polyaxial holes 330, 430 occurs in the shaft of both lateral plates. The staggered hole pattern in the shaft provides increased pull-out resistance and helps to prevent new linear fracture lines in the metaphyseal and diaphyseal regions. Two DCP slots 332 break the stacked hole pattern at the 1st and 6th holes in the narrow plate (FIG. 15), which may be useful in non-unions and osteotomies.

In the broad plate 900, the polyaxial holes 430 follow the three-hole diagonal pattern, described with reference to FIG. 14, along the entire length of the shaft, nominally angled parallel to the center row of holes 430 but can be targeted inwards or outwards in order to dodge other implants such as total hip or knee arthroplasties.

Figure 17:
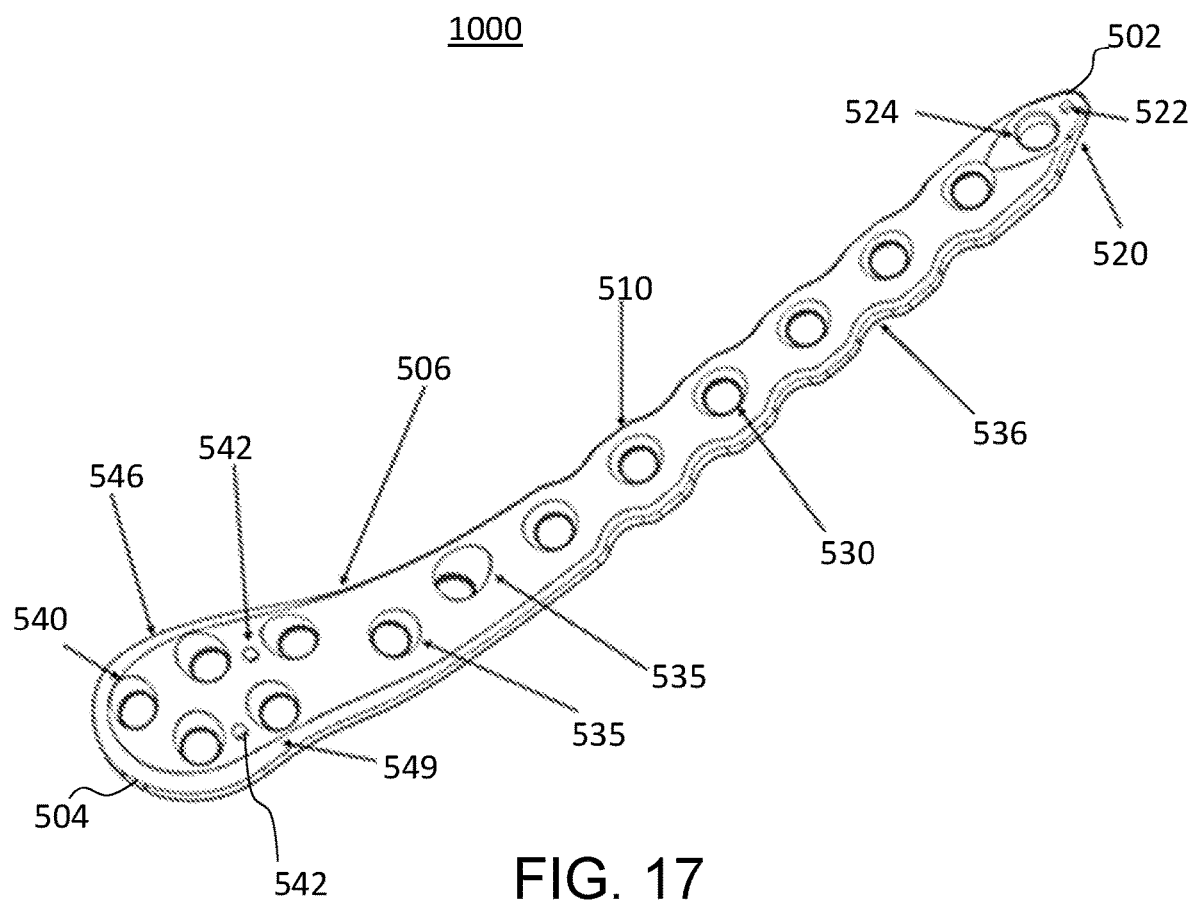
FIG. 17 is a perspective view of another embodiment of a medial locking plate.
Figure 18:
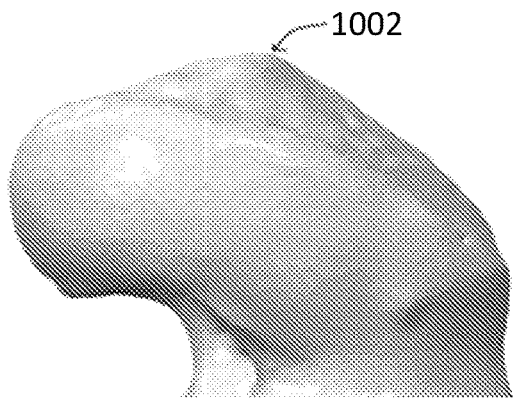
FIG. 18 is a perspective view of the epicondylar ridge on the end of a femur.
Figure 19:
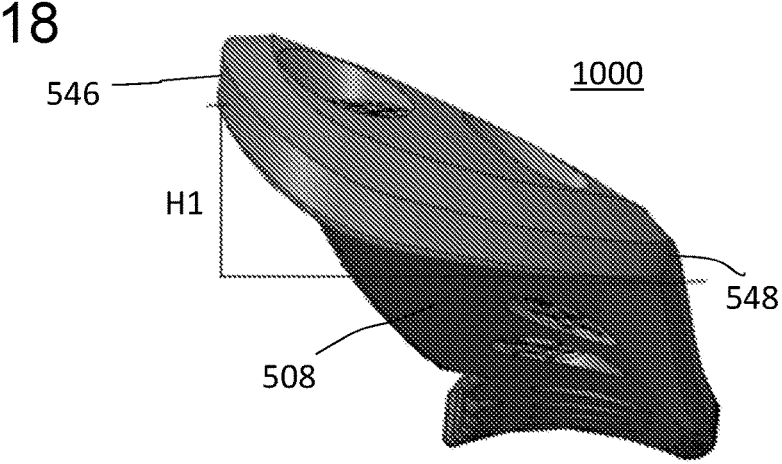
FIG. 19 illustrates the distal portion of the medial plate shown in FIG. 17.
Figure 20:
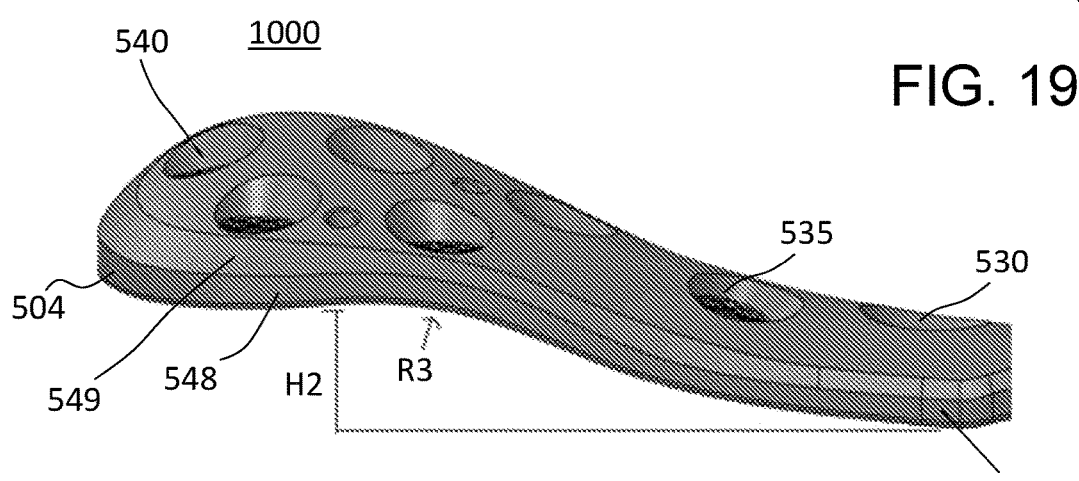
FIG. 20 is a side view of a portion of the medial plate shown in FIG. 17.

Turning now to FIG. 17, the medial locking plate 1000 is similar to plate 500 shown in FIG. 8 and like elements are numbered the same. Medial locking plate 1000 may be advantageous in that the bottom surface 508 of the plate 1000 in contact with bone is anatomically contoured to abut the corresponding contours of the adjacent bone. For example, FIG. 18 illustrates the epicondylar ridge 1002 of the medial condyle, which is a bony protrusion located on the medial side of the femur's distal end. In order to accommodate the epicondylar ridge 1002, the plate 1000 may include one or more of a raised posterior edge H1, an anterior radius R3, and a raised height H2. As shown in FIG. 19, the posterior edge 546 may be raised relative to the anterior edge 548 to conform to the average height of the epicondylar ridge 1002 of the medial condyle. For example, the posterior edge 546 may be higher than anterior edge 548 by a height H1. Height H1 of the raised posterior edge 546 may be about 10-14 mm, or about 12 mm, as compared to the anterior edge 548. Turning to FIG. 20, the bottom surface 508 of the plate 1000 may include an anterior radius R3. The anterior radius R3, for example, along the anterior edge 548, may be contoured to the distal end of the femur. For example, the radius R3 may range from about 28-32 mm, or about 30 mm. In addition, the height H2 of the distal portion 504 may be raised relative to the shaft 510 of the plate 1000. For example, the height H2 may be about 9-10 mm, or about 9.5 mm. The anterior radius R3 and raised height H2 relative to the plate shaft 510 are designed to conform to the average size of the anteromedial third of the medial condyle. These unique anatomic features provide for a better fit to the bone and may provide better patient outcomes.

Plate 1000 may include holes 530, 540, kickstand holes 535, articulated tensioning device (ATD) hole 524, and k-wire holes 522, 542 as already described herein. The holes 530, 540 may be locking holes, such as polyaxial locking holes. In particular, the locking holes may be thread-forming holes such that the fastener locks to the plate 1000 when inserted therein. The locking holes 530, 540, for example, provided in all portions of the plate 1000, permit the creation of a fixed angle construct which helps to prevent both *varus* collapse and screw backout, even in cases of osteoporosis.

The medial locking plate 1000 may be inserted through an incision over the anteromedial aspect of the distal femur or an S-shaped incision on the posterior side of the knee joint. The plate 1000 is designed to sit on the most anterior third of the medial condyle, directly on top of the medial epicondyle. Plate 1000 may provide the same types of features as the narrow and broad lateral plates including all polyaxial locking holes 540 in the distal cluster and polyaxial locking holes 530 along the shaft 510 and two polyaxial locking kickstand strut holes 535 designed to target the strong cortical bone in the posterolateral cortex of the condyle and promote angular stability. The thickness of the plate 1000 may vary from about 3.0 mm proximally to about 2.25 mm distally with the transition occurring in the metaphyseal region of the plate 1000.

Unlike other plates that may lead to misplacement or are improperly contoured, the plates described in embodiments herein may have raised contours on their respective posterior sides to sit more flush on the condylar anatomy and provide surgeons with a way to key in the plate in the correct location. By having a large number of options for fixation along the plates, helps in preventing *varus* collapse and loss of fixation in poor bone quality. Many options for points of fixation become even more important in highly comminuted articular blocks or when other existing implants may need to be avoided.

One skilled in the art will appreciate that the embodiments discussed above are non-limiting. While bone plates may be described as suitable for a particular approach (e.g., medial or lateral), one skilled in the art will appreciate that the bone plates can be used for multiple approaches. In addition, while bone plates are described as having particular holes (e.g., locking or non-locking), one skilled in the art will appreciate that any of the bone plates can include locking, non-locking or a combination of locking and non-locking holes. In addition to the bone plates, screws and instruments described above, one skilled in the art will appreciate that these described features can be used with a number of trauma treatment instruments and implants, including external fixators, ring fixators, rods, and other plates and screws. It will also be appreciated that one or more features of one embodiment may be partially or fully incorporated into one or more other embodiments described herein.

What is claimed is:

1. A system for treating a fracture in a bone comprising:
a bone plate configured to engage the bone, the bone plate extending along a longitudinal axis and comprising a proximal portion, a shaft, and a distal portion,
the shaft comprising a plurality of holes, the plurality of holes including a first repeating pattern of holes and a second repeating pattern of holes,
wherein the shaft further comprises anterior and posterior sidewalls each defining at least one waisted edge scallop, and
wherein a center point of a waisted edge scallop on the anterior side wall and a center point of a waisted edge scallop on the posterior side wall are aligned along an axis that is perpendicular to the longitudinal axis of the bone plate.

2. The system of claim 1 further comprising at least one fastener received through the plurality of holes of the shaft; and at least one fastener received through the plurality of distal holes of the distal portion.

3. The system of claim 1, wherein the waisted edge scallop of the anterior side wall defines a first indentation and the waisted edge scallop of the posterior sidewall defines a second indentation.

4. The system of claim 3, wherein the first and second indentions are generally aligned with a first center hole of the first repeating pattern.

5. The system of claim 4, the first repeating pattern of holes having a first virtual line segment connecting center points of all of the first repeating pattern of holes, the second repeating pattern of holes having a second virtual line segment connecting center points of all of the second repeating pattern of holes, and a third virtual line segment that connects a center point for a radius of the first indentation to a center point for a radius of the second indentation.

6. The system of claim 1, wherein the waisted edge scallops are in the form of undulating scallops which result in a shaft profile that continually varies in overall width.

7. The system of claim 1, wherein the bone plate comprises a plurality of kickstand holes, the kickstand holes separated from one another and oriented in different directions.

8. The system of claim 1, wherein the proximal portion comprises a tapered tip.

9. The system of claim 1, wherein the first repeating pattern includes a first center hole and the second repeating pattern includes a second center hole, and the center points of the first and second center holes are aligned generally along the longitudinal axis of the plate.

10. The system of claim 1, wherein the distal portion comprises a plurality of distal holes and a posterior side and an anterior side and the posterior side of the distal portion is raised relative to the anterior side of the distal portion.

11. A system for treating a fracture in a bone comprising:
a bone plate configured to engage the bone, the bone plate extending along a longitudinal axis and comprising a proximal portion, a shaft, and a distal portion,
the shaft comprising a plurality of holes, the plurality of holes including a first repeating pattern of holes and a second repeating pattern of holes, the first repeating pattern of holes having a first virtual line segment connecting center points of all of the first repeating pattern of holes, the second repeating pattern of holes having a second virtual line segment connecting center points of all of the second repeating pattern of holes,
wherein the first repeating pattern includes a first center hole and the second repeating pattern includes a second center hole,
wherein the shaft further comprises an anterior sidewall defining waisted edge scallops,
wherein a waisted edge scallop of the anterior side wall defines a first indentation,
wherein a third virtual line segment connects a center point of the first center hole to a center point of the first indentation, and
wherein the third virtual line segment is perpendicular to the longitudinal axis of the bone plate.

12. The system of claim 11 further comprising at least one fastener received through the plurality of holes of the shaft.

13. The system of claim 11, wherein the shaft further comprises a posterior sidewall defining waisted edge scallops.

14. The system of claim 11, wherein a waisted edge scallop of the posterior sidewall defines a second indentation.

15. The system of claim 11, wherein the first and second indentions are generally aligned with the first center hole of the first repeating pattern.

16. The system of claim 11, wherein a fourth virtual line segment connects a center point for a radius of the first indentation to a center point for a radius of the second indentation.

17. The system of claim 11, wherein the waisted edge scallops are in the form of undulating scallops which result in a shaft profile that continually varies in overall width.

18. The system of claim 11, wherein the bone plate comprises a plurality of kickstand holes, the kickstand holes separated from one another and oriented in different directions.

19. The system of claim 11, wherein the proximal portion comprises a tapered tip.

20. The system of claim 11, wherein the distal portion comprises a plurality of distal holes and a posterior side and an anterior side, wherein the posterior side of the distal portion is raised relative to the anterior side of the distal portion.

* * * * *